(12) United States Patent
O'Shea et al.

(10) Patent No.: US 11,963,676 B2
(45) Date of Patent: Apr. 23, 2024

(54) AUTONOMOUS METHODS AND SYSTEMS FOR TYING SURGICAL KNOTS

(71) Applicant: Activ Surgical, Inc., Boston, MA (US)

(72) Inventors: Liam O'Shea, Westwood, MA (US); Thomas J. Calef, Boston, MA (US); Dana Zitnick, Warwick, RI (US)

(73) Assignee: Activ Surgical, Inc., Boston, MA (US)

( * ) Notice: Subject to any disclaimer, the term of this patent is extended or adjusted under 35 U.S.C. 154(b) by 350 days.

(21) Appl. No.: 17/221,685

(22) Filed: Apr. 2, 2021

(65) Prior Publication Data
US 2021/0361281 A1    Nov. 25, 2021

Related U.S. Application Data

(63) Continuation of application No. PCT/US2019/056484, filed on Oct. 16, 2019.

(60) Provisional application No. 62/746,303, filed on Oct. 16, 2018.

(51) Int. Cl.
*A61B 17/04* (2006.01)
*A61B 34/00* (2016.01)
*A61B 34/30* (2016.01)

(52) U.S. Cl.
CPC ...... *A61B 17/0469* (2013.01); *A61B 17/0467* (2013.01); *A61B 34/30* (2016.02); *A61B 34/71* (2016.02); *A61B 2017/0474* (2013.01)

(58) Field of Classification Search
CPC ............ A61B 17/0469; A61B 17/0467; A61B 17/0483; A61B 34/30; A61B 34/70; A61B 34/71; A61B 2017/0474
See application file for complete search history.

(56) References Cited

U.S. PATENT DOCUMENTS

| | | | |
|---|---|---|---|
| 4,596,249 A | 6/1986 | Freda et al. |
| 5,254,126 A | 10/1993 | Filipi et al. |
| 5,480,406 A | 1/1996 | Nolan et al. |
| 5,545,170 A | 8/1996 | Hart |
| 5,797,927 A | 8/1998 | Yoon |

(Continued)

FOREIGN PATENT DOCUMENTS

| | | |
|---|---|---|
| WO | WO-2010096447 A2 | 8/2010 |
| WO | WO-2010096453 A1 | 8/2010 |

(Continued)

OTHER PUBLICATIONS

PCT/US2019/056484 International Search Report and Written Opinion dated Apr. 23, 2020.

(Continued)

*Primary Examiner* — Kelly J Bekker
*Assistant Examiner* — Mohammed S Adam
(74) *Attorney, Agent, or Firm* — Wilson Sonsini Goodrich & Rosati

(57) ABSTRACT

A robotic suture knot tying system includes a first robotic arm, a second robotic arm, a suturing device including a suturing end effector operatively coupled to the first robotic arm, and a suture handling device operatively coupled to the second robotic arm. The system also includes a control system operatively coupled to the first robotic arm, the second robotic arm, the suturing device, and the suture handling device and configured to control operation thereof to cooperatively perform a suture knot tying procedure on a patient.

19 Claims, 35 Drawing Sheets

(56) References Cited

U.S. PATENT DOCUMENTS

| | | |
|---|---|---|
| 5,808,665 A | 9/1998 | Green |
| 5,876,325 A | 3/1999 | Mizuno et al. |
| 5,938,668 A | 8/1999 | Scirica et al. |
| 5,954,731 A | 9/1999 | Yoon |
| 6,001,108 A | 12/1999 | Wang et al. |
| 6,126,665 A * | 10/2000 | Yoon .............. A61B 17/062 606/144 |
| 6,183,485 B1 | 2/2001 | Thomason et al. |
| 6,206,894 B1 | 3/2001 | Thompson et al. |
| 6,223,100 B1 | 4/2001 | Green |
| 6,309,397 B1 | 10/2001 | Julian et al. |
| 6,325,808 B1 | 12/2001 | Bernard et al. |
| 7,959,557 B2 | 6/2011 | Weitzner et al. |
| 8,052,636 B2 | 11/2011 | Moll et al. |
| 8,257,303 B2 | 9/2012 | Moll et al. |
| 8,395,342 B2 | 3/2013 | Prisco |
| 8,406,859 B2 | 3/2013 | Zuzak et al. |
| 8,617,102 B2 | 12/2013 | Moll et al. |
| 8,792,098 B2 | 7/2014 | Dewald et al. |
| 8,823,790 B2 | 9/2014 | Dunn et al. |
| 8,891,087 B2 | 11/2014 | Zuzak et al. |
| 9,072,445 B2 | 7/2015 | Berguer et al. |
| 9,149,281 B2 | 10/2015 | Bonutti |
| 9,155,544 B2 | 10/2015 | Bonutti |
| 9,186,053 B2 | 11/2015 | Viola |
| 9,192,395 B2 | 11/2015 | Bonutti |
| 9,198,578 B2 | 12/2015 | Zuzak et al. |
| 9,220,570 B2 | 12/2015 | Kim et al. |
| 9,226,673 B2 | 1/2016 | Ferguson, Jr. et al. |
| 9,226,811 B2 | 1/2016 | Abuzaina |
| 9,271,658 B2 | 3/2016 | Ferguson, Jr. et al. |
| 9,402,986 B2 | 8/2016 | Bell et al. |
| 9,457,168 B2 | 10/2016 | Moll et al. |
| 9,561,028 B1 | 2/2017 | Fan |
| 9,585,600 B2 | 3/2017 | Sharonov |
| 9,622,662 B2 | 4/2017 | Zuzak et al. |
| 9,662,018 B2 | 5/2017 | Stopek |
| 9,788,903 B2 | 10/2017 | Kim et al. |
| 9,820,736 B1 | 11/2017 | Fan |
| 10,058,256 B2 | 8/2018 | Chen et al. |
| 10,089,737 B2 | 10/2018 | Krieger et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,278,220 B2 | 3/2022 | Tucker et al. |
| 2001/0041916 A1 | 11/2001 | Bonutti |
| 2003/0083650 A1 | 5/2003 | Wang et al. |
| 2003/0083651 A1 | 5/2003 | Wang et al. |
| 2004/0073257 A1 | 4/2004 | Spitz |
| 2004/0176751 A1 | 9/2004 | Weitzner et al. |
| 2004/0193146 A1 | 9/2004 | Lee et al. |
| 2005/0090840 A1 | 4/2005 | Gerbino et al. |
| 2006/0020272 A1 | 1/2006 | Gildenberg |
| 2007/0213749 A1 | 9/2007 | Kogasaka et al. |
| 2007/0232855 A1 | 10/2007 | Weitzner et al. |
| 2007/0239178 A1 | 10/2007 | Weitzner et al. |
| 2007/0250072 A1 | 10/2007 | Weitzner et al. |
| 2007/0250097 A1 | 10/2007 | Weitzner et al. |
| 2008/0009900 A1 | 1/2008 | Heaven et al. |
| 2008/0015408 A1 | 1/2008 | Paolitto et al. |
| 2008/0177281 A1 | 7/2008 | Weitzner et al. |
| 2009/0292300 A1 | 11/2009 | Hamilton et al. |
| 2010/0081875 A1 | 4/2010 | Fowler et al. |
| 2012/0095354 A1 | 4/2012 | Dunn et al. |
| 2012/0130405 A1 | 5/2012 | Cohn et al. |
| 2012/0191133 A1 | 7/2012 | Ferree |
| 2013/0274596 A1 | 10/2013 | Azizian et al. |
| 2014/0039527 A1 | 2/2014 | Avelar et al. |
| 2014/0100587 A1 | 4/2014 | Farritor et al. |
| 2014/0243850 A1 | 8/2014 | Sadaka |
| 2014/0276944 A1 | 9/2014 | Farritor et al. |
| 2015/0005622 A1 | 1/2015 | Zhao et al. |
| 2015/0012016 A1 | 1/2015 | Stone |
| 2015/0289919 A1 | 10/2015 | Privitera et al. |
| 2016/0000423 A1 | 1/2016 | Shields et al. |
| 2016/0206391 A1 | 7/2016 | Deodhar |
| 2016/0296225 A1 | 10/2016 | Rohl et al. |
| 2017/0333030 A1 | 11/2017 | Bourland, III et al. |
| 2019/0000561 A1 | 1/2019 | Decker et al. |
| 2019/0133571 A1 | 5/2019 | Racenet et al. |
| 2019/0175166 A1* | 6/2019 | Foerster ............ A61B 17/0469 |
| 2019/0206565 A1 | 7/2019 | Shelton, IV |
| 2019/0282226 A1 | 9/2019 | Epstein et al. |
| 2020/0305721 A1 | 10/2020 | Chen et al. |
| 2021/0030277 A1 | 2/2021 | Ferguson, Jr. et al. |
| 2021/0259678 A1 | 8/2021 | O'Shea et al. |
| 2021/0259680 A1 | 8/2021 | O'Shea et al. |
| 2021/0275167 A1 | 9/2021 | Bedoya et al. |
| 2021/0282654 A1 | 9/2021 | Cha et al. |
| 2023/0000565 A1 | 1/2023 | Pickett et al. |

FOREIGN PATENT DOCUMENTS

| | | |
|---|---|---|
| WO | WO-2012096878 A2 | 7/2012 |
| WO | WO-2014005139 A2 | 1/2014 |
| WO | WO-2014152753 A1 | 9/2014 |
| WO | WO-2016061052 A1 | 4/2016 |
| WO | WO-2016153741 A1 | 9/2016 |
| WO | WO-2017075602 A1 | 5/2017 |
| WO | WO-2019045971 A1 | 3/2019 |
| WO | WO-2020006454 A1 | 1/2020 |
| WO | WO-2020055795 A1 | 3/2020 |
| WO | WO-2020055797 A1 | 3/2020 |
| WO | WO-2020081651 A1 | 4/2020 |
| WO | WO-2021146339 A1 | 7/2021 |
| WO | WO-2022029308 A1 | 2/2022 |
| WO | WO-2022058499 A1 | 3/2022 |

OTHER PUBLICATIONS

Dunn, et al. Laser speckle contrast imaging in biomedical optics. Journal of Biomedical Optics 15(1), 011109 (Jan./Feb. 2010).

Holstein-Rathlou et al. Nephron blood flow dynamics measured by laser speckle contrast imaging. Am J Phsiol Renal Physiol 300: F319-F329, 2011.

PCT/US19/50308 International Search Report & Written Opinion dated Nov. 19, 2019.

PCT/US19/50311 International Search Report & Written Opinion dated Nov. 20, 2019.

PCT/US21/13309 International Search Report and Written Opinion dated Mar. 31, 2021.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

U.S. Appl. No. 17/191,200 Office Action dated Jun. 7, 2023.

U.S. Appl. No. 17/191,407 Office Action dated Nov. 16, 2023.

* cited by examiner

AUTONOMOUS METHODS AND SYSTEMS FOR TYING SURGICAL KNOTS

CROSS REFERENCE TO RELATED APPLICATION

This application is a continuation of International Application No. PCT/US2019/056484, filed Oct. 16, 2019, which application claims priority from U.S. Provisional Patent Application No. 62/746,303 filed on Oct. 16, 2018, which applications are incorporated herein by reference in their entirety for all purposes.

BACKGROUND

The present application relates generally to autonomous surgical procedures and, more particularly, to methods and apparatus for surgical knot tying.

Suturing is used to close the edges of a wound or incision and to repair damaged tissue during surgery. Sutures can be applied using a suturing device having a needle, which can be manipulated to draw a suture through the tissue at the edges of the incision. The suture can be tightened to draw the edges of the tissue together, and then knotted and the suture tail trimmed. Suture knots can comprise, e.g., one or more square knots made in a row at different points.

BRIEF SUMMARY

A robotic suture knot tying system in accordance with one or more embodiments includes a first robotic arm, a second robotic arm, a suturing device including a suturing end effector operatively coupled to the first robotic arm, a suture handling device operatively coupled to the second robotic arm, and a control system. The control system is operatively coupled to the first robotic arm, the second robotic arm, the suturing device, and the suture handling device and configured to control operation thereof to cooperatively perform a suture knot tying procedure on a patient.

A method in accordance with one or more embodiments is disclosed for tying a surgical knot on tissue of a patient using a robotic suture knot tying system. The robotic suture knot tying system includes a suturing device having a suturing end effector and a suture handling device having first and second suture grasping instruments. The method includes the steps of: (a) throwing a stitch at a target location on the tissue patient using the suturing end effector to form first and second suture lines extending out of the target location; (b) grasping the first suture line with one of the first and second suture grasping instruments and cutting the first suture line; (c) manipulating the suturing end effector and the first and second suture grasping instruments to tie a suture knot from the first and second suture lines; and (d) tightening the suture knot onto the tissue using the first and second suture grasping instruments.

A robotic suture knot tying system in accordance with one or more embodiments includes a first robotic arm, a second robotic arm, a suturing device including a suturing end effector operatively coupled to the first robotic arm, and a suture handling device operatively coupled to the second robotic arm. The suture handling device comprises: (a) an elongated tubular housing having a proximal end coupled to the second robotic arm and an opposite distal end, the housing including a first channel, a second channel, and a third channel therein, each channel extending longitudinally along the length of the tubular housing; (b) a first suture grasping instrument in the first channel of the housing, the first suture grasping instrument having an end effector that can be actuated to extend outwardly from the distal end of the housing to grasp and manipulate a suture; (c) a second suture grasping instrument in the second channel of the housing, the second suture grasping instrument having an end effector that can be actuated to extend outwardly from the distal end of the housing to grasp and manipulate the suture; and (d) a laparoscope in the third channel in the tubular housing. The robotic suture knot tying system also includes a control system operatively coupled to the first robotic arm, the second robotic arm, the suturing device, and the suture handling device and being configured to control operation thereof to cooperatively perform a suture knot tying procedure on a patient.

DETAILED DESCRIPTION

Figure 1:
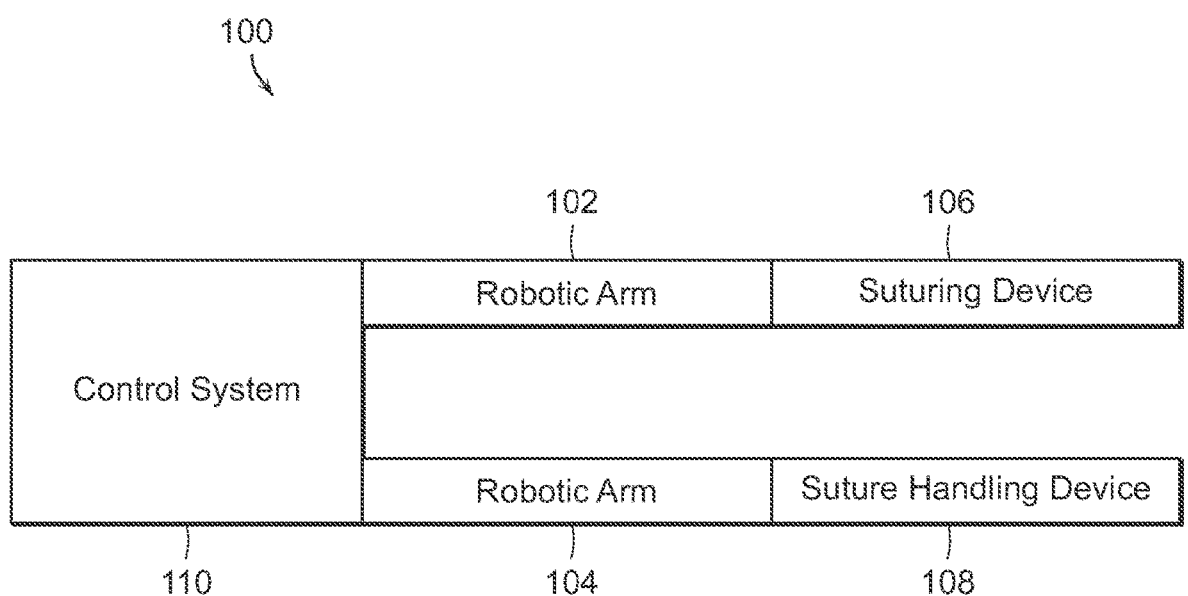
FIG. 1 is a simplified block diagram illustrating an exemplary robotic suturing system in accordance with one or more embodiments.

FIG. 1 is a block diagram schematically illustrating one example of a robotic suturing system 100 that can be used to perform a suturing procedure on a patient lying on an operating table during surgery, including autonomous suture knot tying in accordance with one or more embodiments.

The system includes a first robotic arm 102 operatively coupled to a suturing device 106. The system also includes a second robotic arm 104 operatively coupled to a suture handling device 108. Each robot arm is connected to a computer control system 110, which controls movement of the robot arms and operation of the suturing device 106 and the suture handling device 108.

Examples of robotic arms that can be configured for use in the suturing system include those available from KUKA Robotics, Medineering Surgical Robotics, and ABB Robotics, among others.

Figure 2:
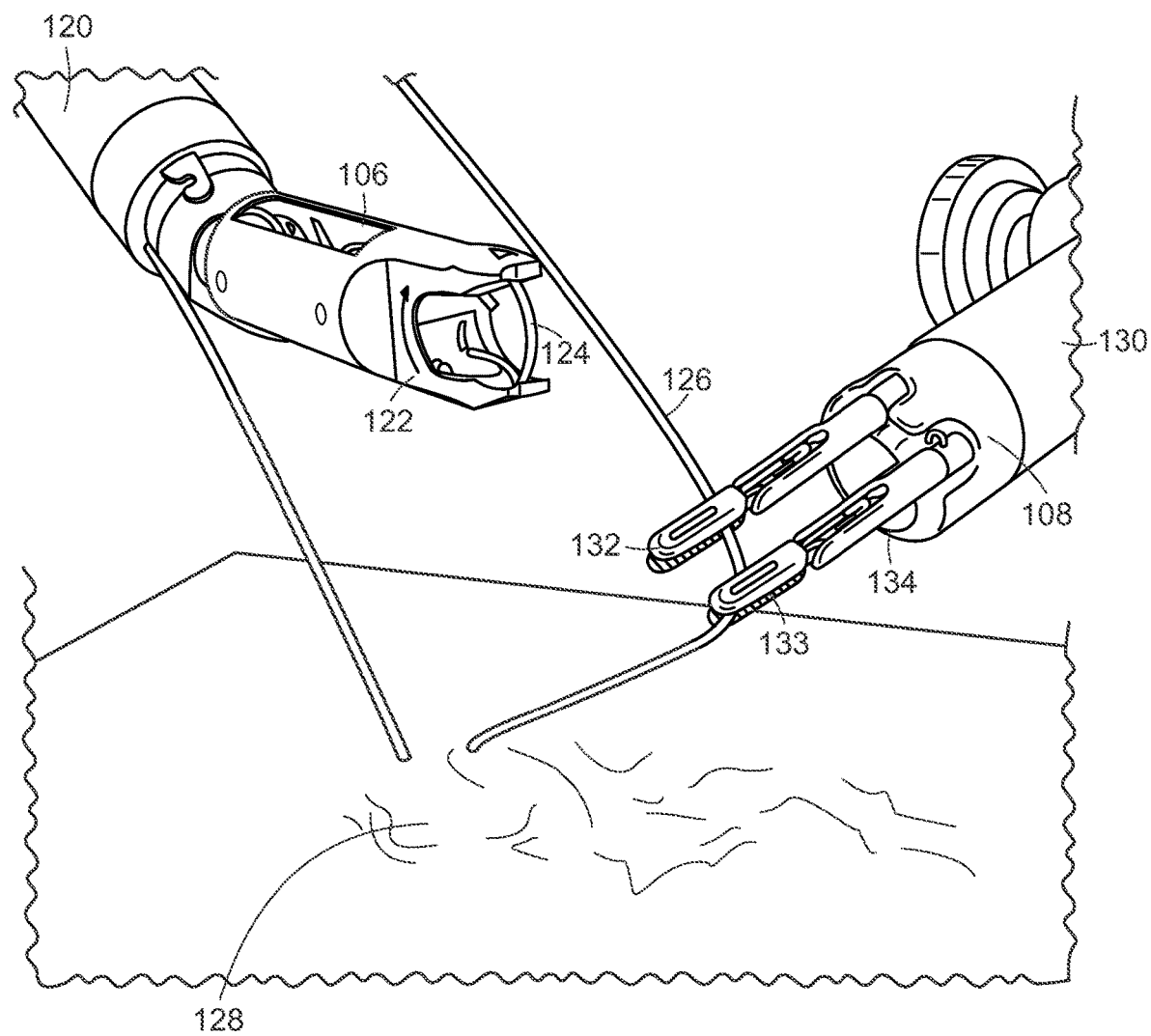
FIGS. 2 and 3 illustrate operation of the suturing system in a suturing procedure.
Figure 3:
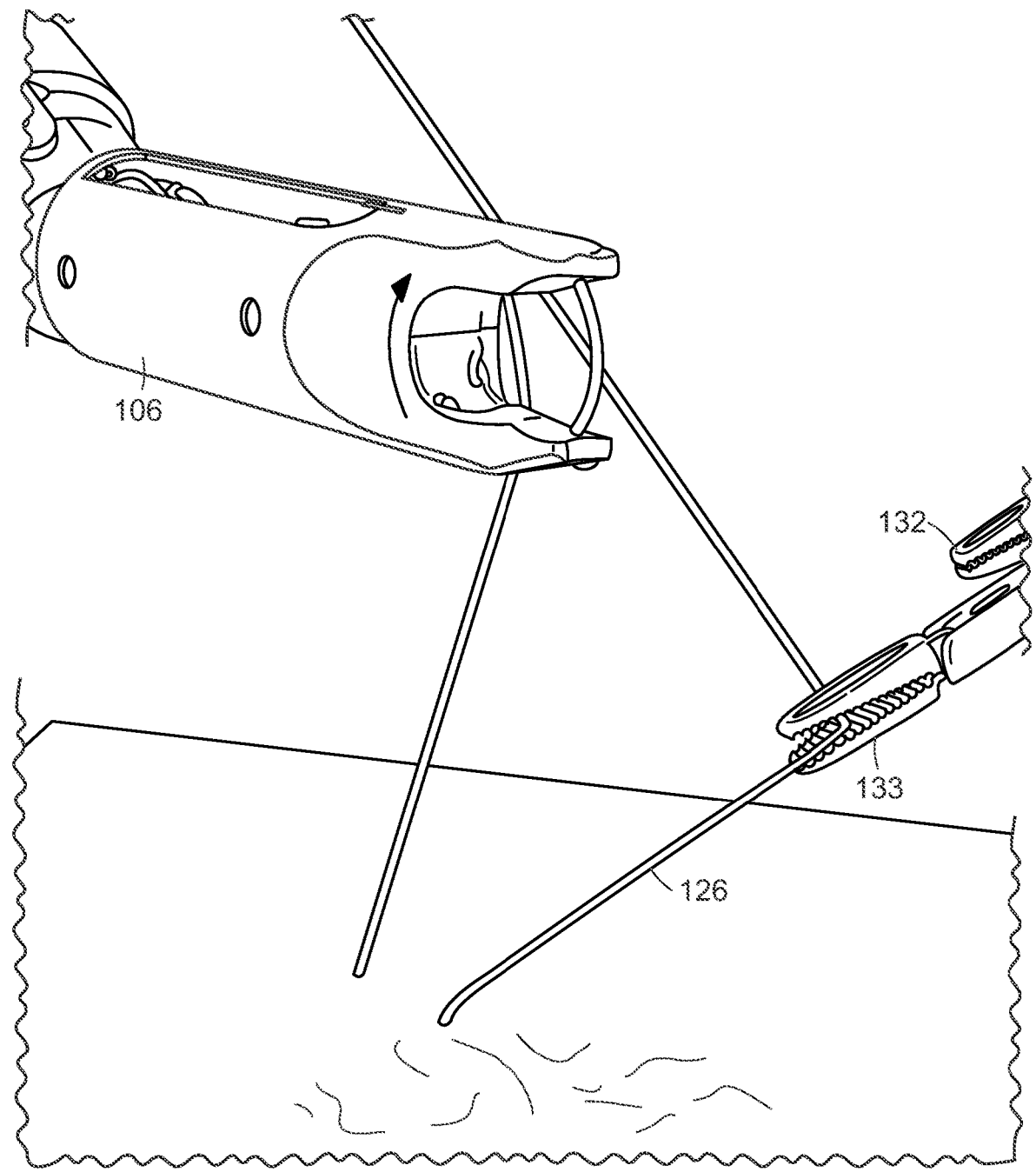

FIGS. 2 and 3 illustrate operation of the suturing device 106 and the suture handling device 108 in a suturing procedure. The suturing device 106 includes a tubular housing 120 having a proximal end (not shown) coupled to the first robotic arm 102 and an opposite distal end having a suturing end effector 122. By way of example, the suturing end effector 122 can be an ENDO360 suturing end effector available from EndoEvolution. The suturing end effector 122 includes a curved needle 124 that can be manipulated to draw a suture 126 through tissue 128. The suture handling device 108 works cooperatively with the suturing device 106 to place and knot the suture 126 in the tissue 128 as shown in FIGS. 2 and 3.

The suture handling device 108 includes an elongated tubular housing 130 having a proximal end (not shown) connected to the second robotic arm 104 and an opposite distal end having first and second suture grasping end effectors (or graspers) 132, 133 and a laparoscope (or camera assembly) 134.

The elongated tubular housing 130 includes three internal working channels extending longitudinally along the length of the tubular housing 130. The first and second channels house the first and second suture grasping instruments 132, 133, respectively. The third channel houses the laparoscope 134. The first and second suture grasping instruments 132, 133 and the laparoscope 134 can each be independently extended from and retracted into the tubular housing 130.

Figure 4:
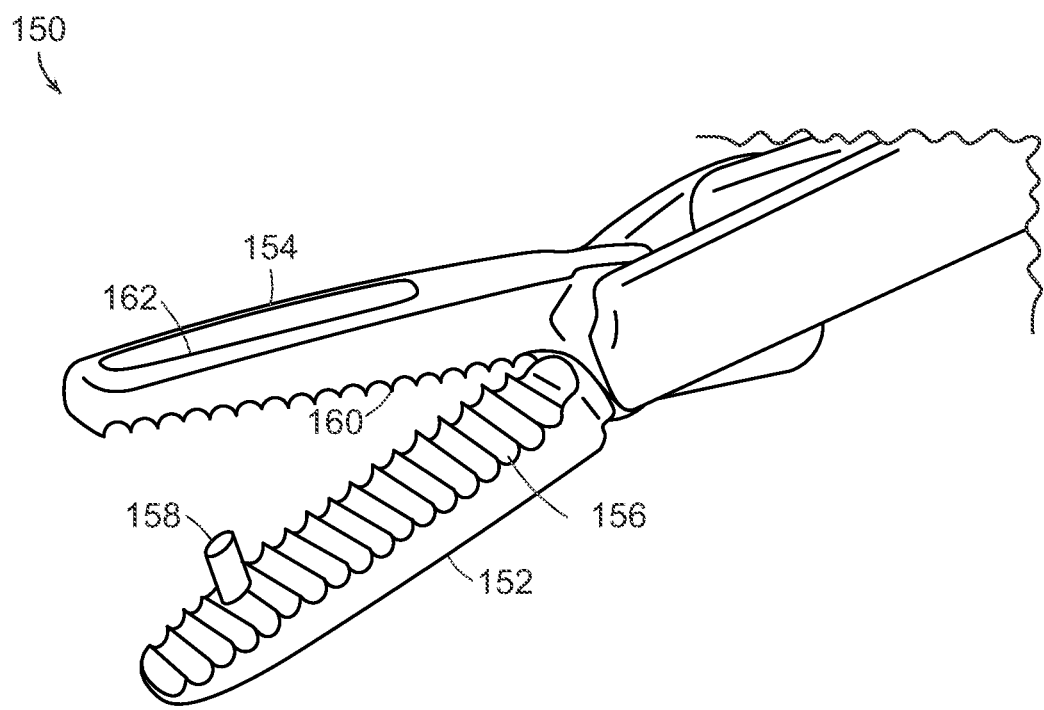
FIG. 4 illustrate an exemplary surgical grasper in the suturing system in accordance with one or more embodiments.

The first and second suture grasping end effectors 132, 133 each include a surgical grasper 150 shown in greater detail in FIG. 4. The surgical grasper 150 includes a jaw assembly comprising a first jaw member 152 pivotally connected to a second jaw member 154.

By way of non-limiting example, each jaw assembly can be a 2-3.5 mm surgical grasper.

The first jaw member 152 has a suture engagement surface 156 and a suture pivot post 158 extending from the suture engagement surface 156 at a distal end of the first jaw member 152.

The second jaw member 154 opposes the first jaw member 152. The second jaw member 154 has a suture engagement surface 160 facing the suture engagement surface 156 of the first jaw member 152. The second jaw member 154 also has an opening 162 in its suture engagement surface at a distal end of the second jaw member 154 sized and arranged to receive the suture pivot post 158.

In accordance with one or more embodiments, the suture engagement surfaces 156, 160 of the first and second jaw members 152, 154 have complementary serrations (e.g., V or U-shaped teeth) to more securely grip the suture.

Figure 5A:
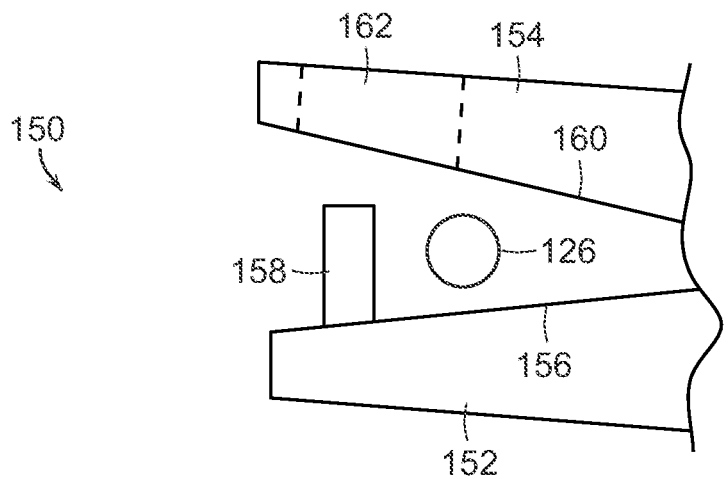
FIGS. 5A-5C illustrate various operating modes of the surgical grasper in accordance with one or more embodiments.
Figure 5B:
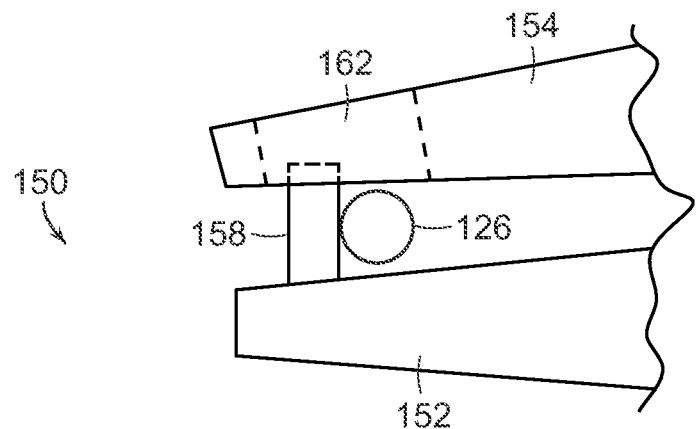
Figure 5C:
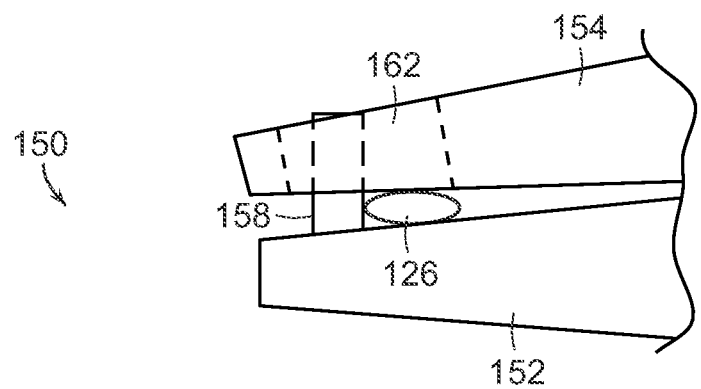

The first and second jaw members 152, 154 are pivotally connected at a proximal end of each jaw member. One or both of the first and second jaw members 152, 154 can be actuated to move relative to the other among at least a first open position, a second suture pulley mode position, and a third suture grasping mode position as illustrated in FIGS. 5A, 5B, and 5C, respectively.

In the first open position (FIG. 5A), the distal ends of the first and second jaw members 152, 154 are separated such that there is a gap between the suture pivot post 158 in the first jaw member 152 and the opening 162 in the second jaw member 154 such that the suture 126 can be inserted in the grasper 150.

In the second suture pulley mode position (FIG. 5B), the distal ends of the first and second jaw members 152, 154 are moved closer together than in the first position. The post 158 engages the opening 162, but the suture engagement surfaces 156, 160 are sufficiently separated to enable the suture 126 to slidably move relative to the grasper 150 using the post 158 as a pivot point and bearing surface.

In the third suture grasping mode position (FIG. 5C), the distal ends of the first and second jaw members 152, 154 are moved closer together than in the second position and the suture engagement surfaces 156, 160 securely grip the suture 126, inhibiting movement of the suture 126 relative to the grasper 150.

FIGS. 2 and 3 illustrate use of the grasping end effectors 132, 133 operating cooperatively with the suture device 106 in a suturing procedure. In FIG. 2, the graspers 132, 133 are operating in the third suture grasping mode, where the suture 126 is securely and fixedly held relative to the graspers. In FIG. 3, the grasper 133 is used in the second suture pulley mode, where the suture 126 slides through the grasper using the post 158 as a pivot point and bearing surface.

Figure 8:
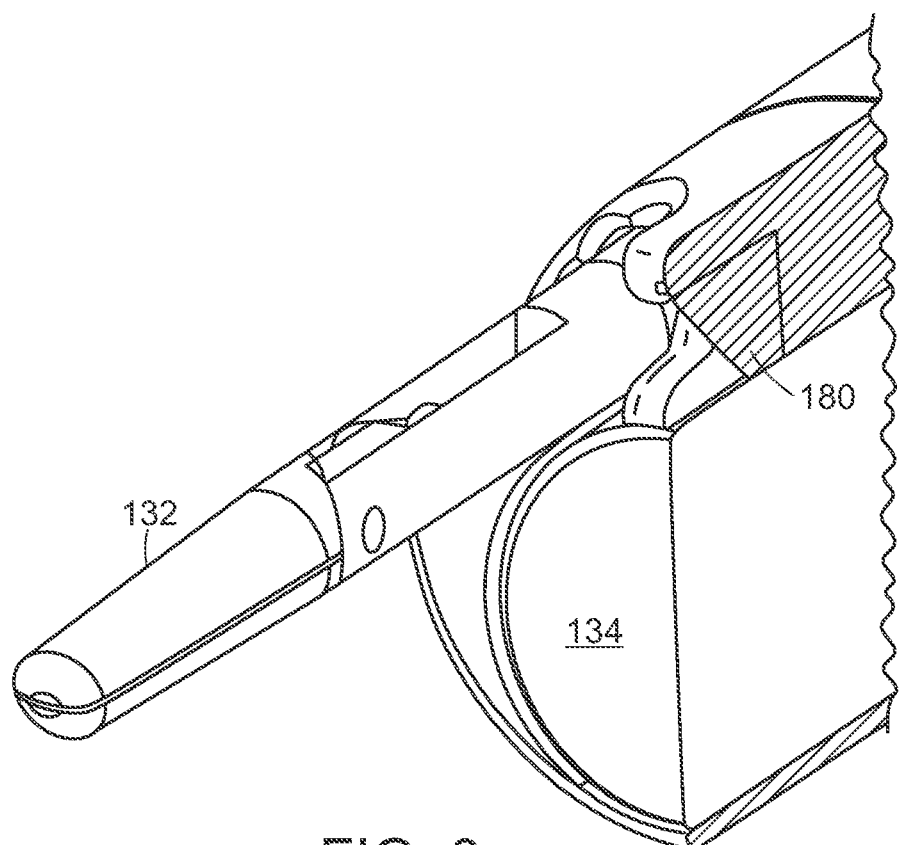
FIG. 8 is a cross-section view of the suture manipulator/cutter device in accordance with one or more embodiments.
Figure 9:
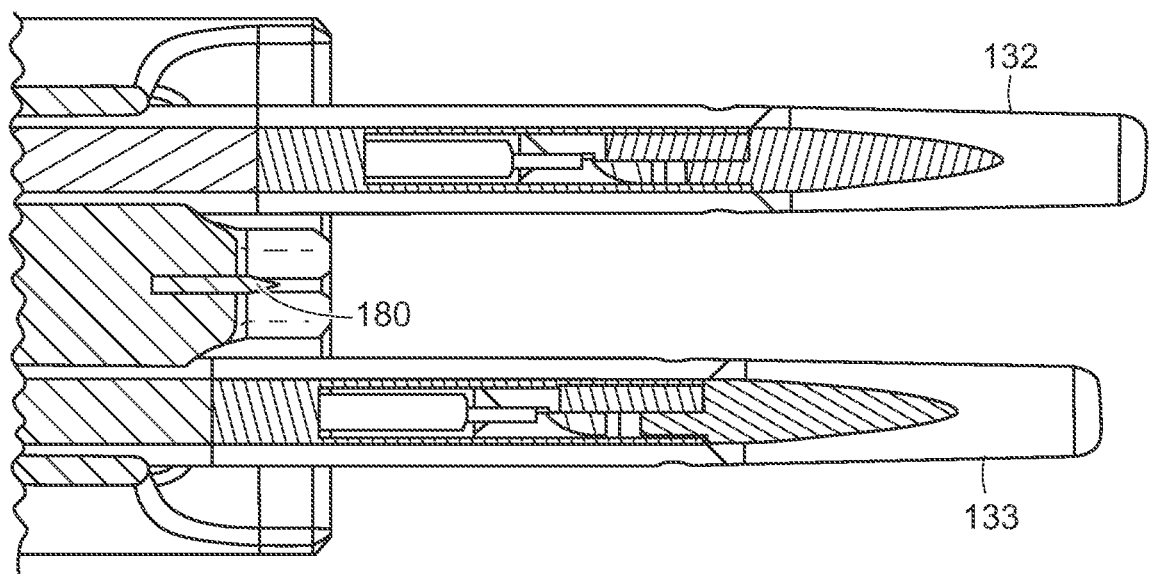
FIG. 9 is another cross-section view the suture manipulator/cutter device in accordance with one or more embodiments.

FIGS. 6-9 illustrate an exemplary process of cutting a suture using a suture cutter in the suturing system in accordance with one or more embodiments. FIGS. 7A and 7B further illustrate the suture manipulator/cutter device with the suture grasping instruments 132, 133 in extended and retracted positions, respectively. FIGS. 8 and 9 are cross-section views of the suture manipulator/cutter device. As shown, a suture cutting blade 180 is recessed in the distal end of the housing 130 at a location between the first and second suture grasping instruments 132, 133. The blade 180 can be fixed to the laparoscope or camera assembly 134. As a safety measure in accordance with one or more embodiments, the blade 180 is recessed within the distal end of the housing 180, thereby guarding against damage from inadvertent contact between the blade 180 and the patient or other equipment.

Movement of the first and second suture grasping instruments 132, 133 is controlled by actuators at the proximal end of the devices 132, 133. The jaw assembly 150 of each suture grasping instruments 132, 133 can be controlled to extend axially from or into the distal end of the housing 130 between a retracted position (shown in FIGS. 6 and 7B) and an extended position (shown in FIGS. 2 and 7A).

Figure 6:
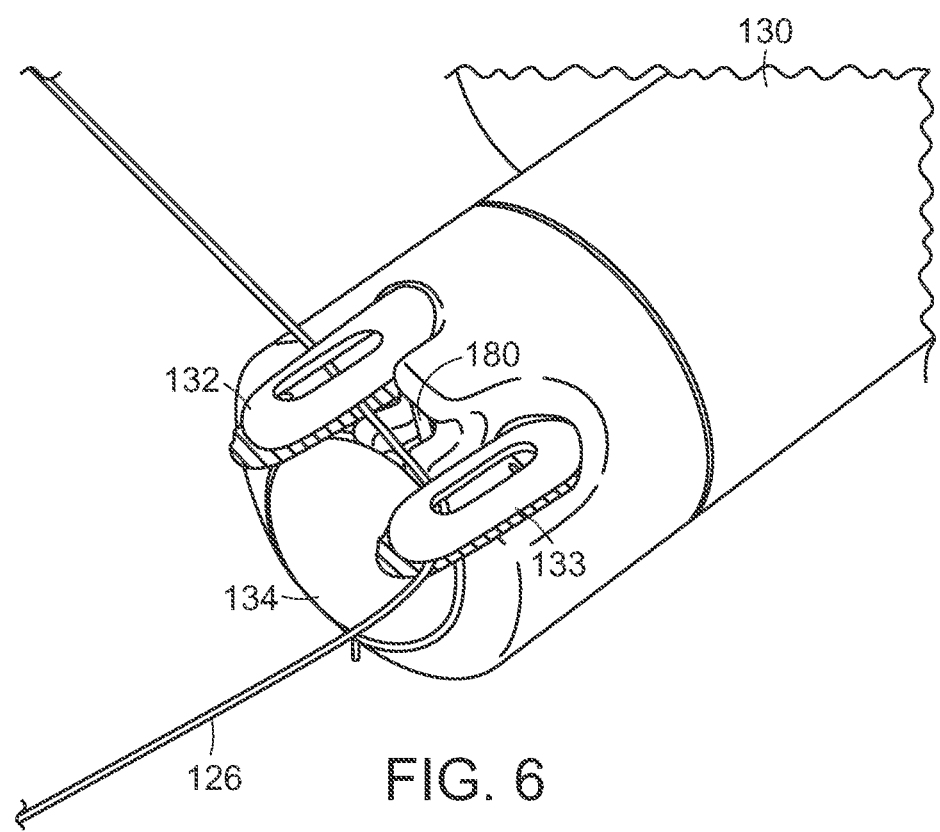
FIG. 6 illustrates the process of cutting a suture using a suture cutter in the suturing system in accordance with one or more embodiments.
Figure 7A:
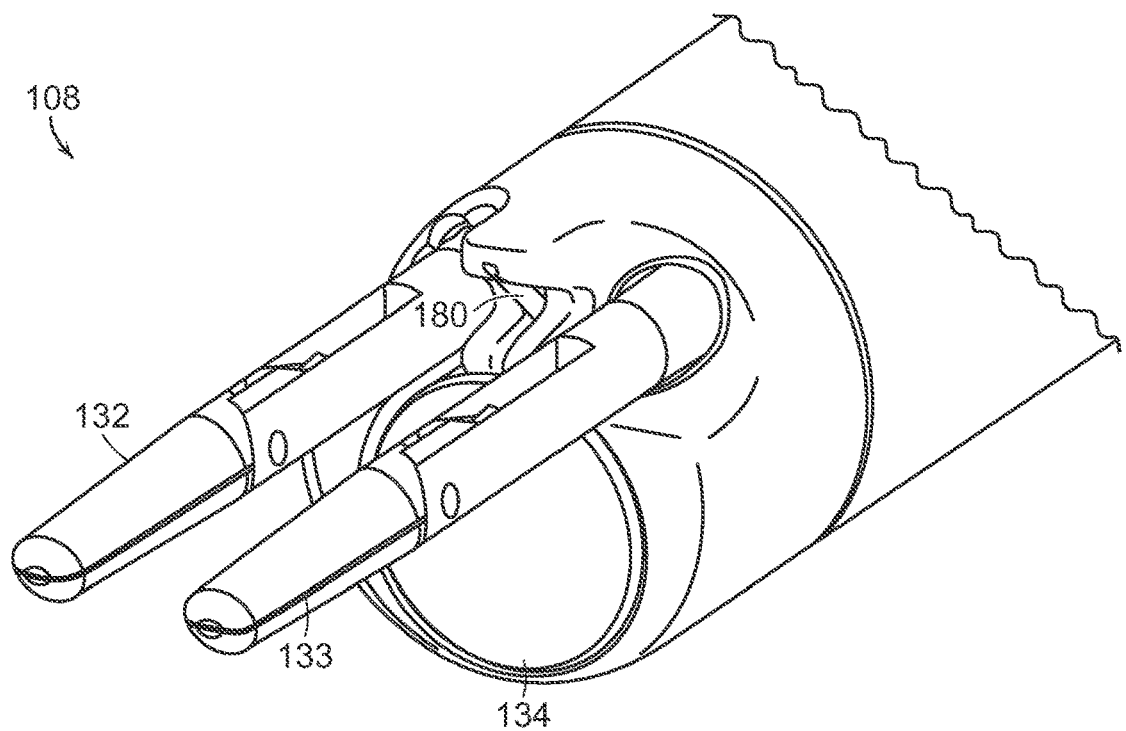
FIGS. 7A and 7B illustrate a suture manipulator/cutter device in accordance with one or more embodiments with suture grasping instruments in extended and retracted positions, respectively.
Figure 7B:
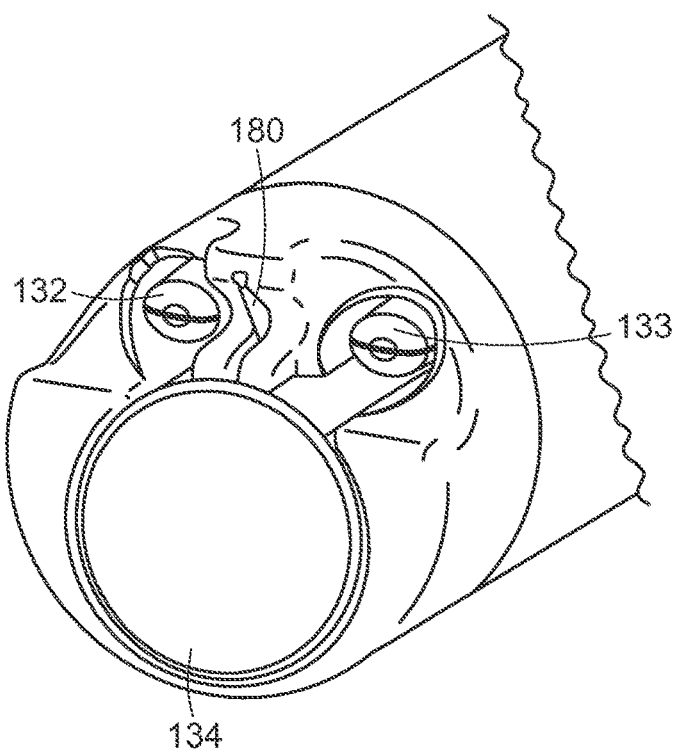

FIGS. 2 and 6 illustrate a process for cutting suture in accordance with one or more embodiments. First, the jaw assemblies 150 of both grasping instrument 132, 133 are extended axially out of the housing 130 and moved by the robotic arm to a position where they each grasp a portion of the suture 126 (FIG. 2). The jaw assemblies 150 grasp the suture 126 at spaced-apart locations on the suture. Next, the jaw assemblies 150 of the suture grasping instruments 132, 133 are actuated to be retracted into the distal end of the housing 130 while grasping portions of the suture (FIG. 6). This retraction of the devices forces the portion of the suture 126 between the grasping instrument 132, 133 to engage and ride along the blade 180, causing the suture to be cut.

The suturing device can be utilized in a variety of robotic surgical equipment, including autonomous robotic surgical systems as well as surgeon-controlled robotic equipment.

One advantage of the suture cutter device integrated in the device 108 having suture graspers is that it avoids the need for a separate device to cut sutures. In other words, the same device 108 used to manipulate suture and work cooperatively with the suturing device 106 to place and knot the suture 126 in the tissue 128, is also used to trim the suture when needed.

In addition, the suture cutter device enables sutures to be quickly and easily grasped and cut. In accordance with one or more embodiments, suture cutter device enables the tail-side of a suture to be cut, leaving enough suture remaining on the needle-side to allow additional suturing after a knot is tied.

FIGS. 10-35 illustrate one example of a process for autonomously tying a square surgical knot in accordance with one or more embodiments using the suturing system described above.

Figure 10:
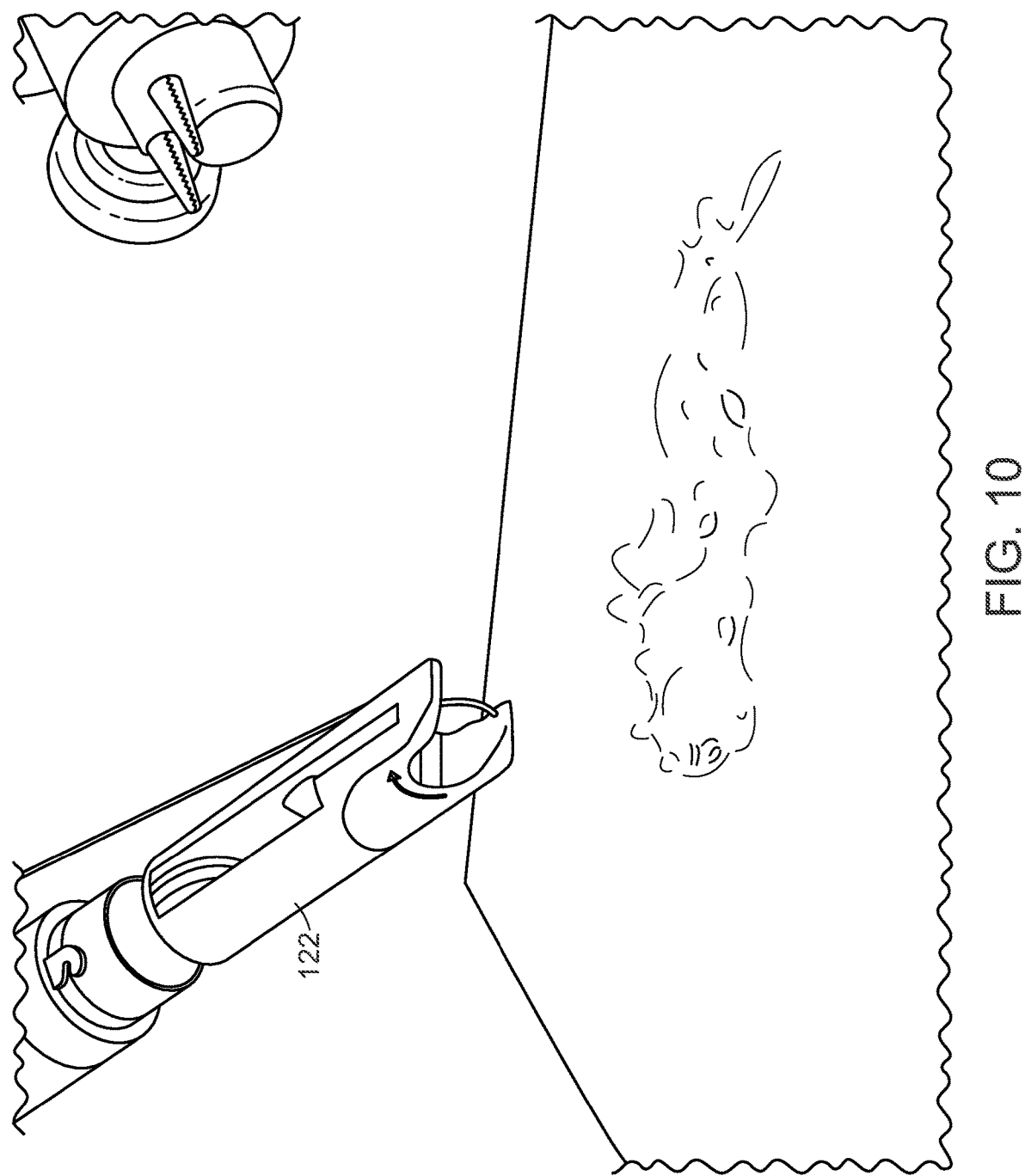
FIGS. 10-35 illustrate one example of a process for autonomously tying square surgical knots using the suturing system in accordance with one or more embodiments.
Figure 11:
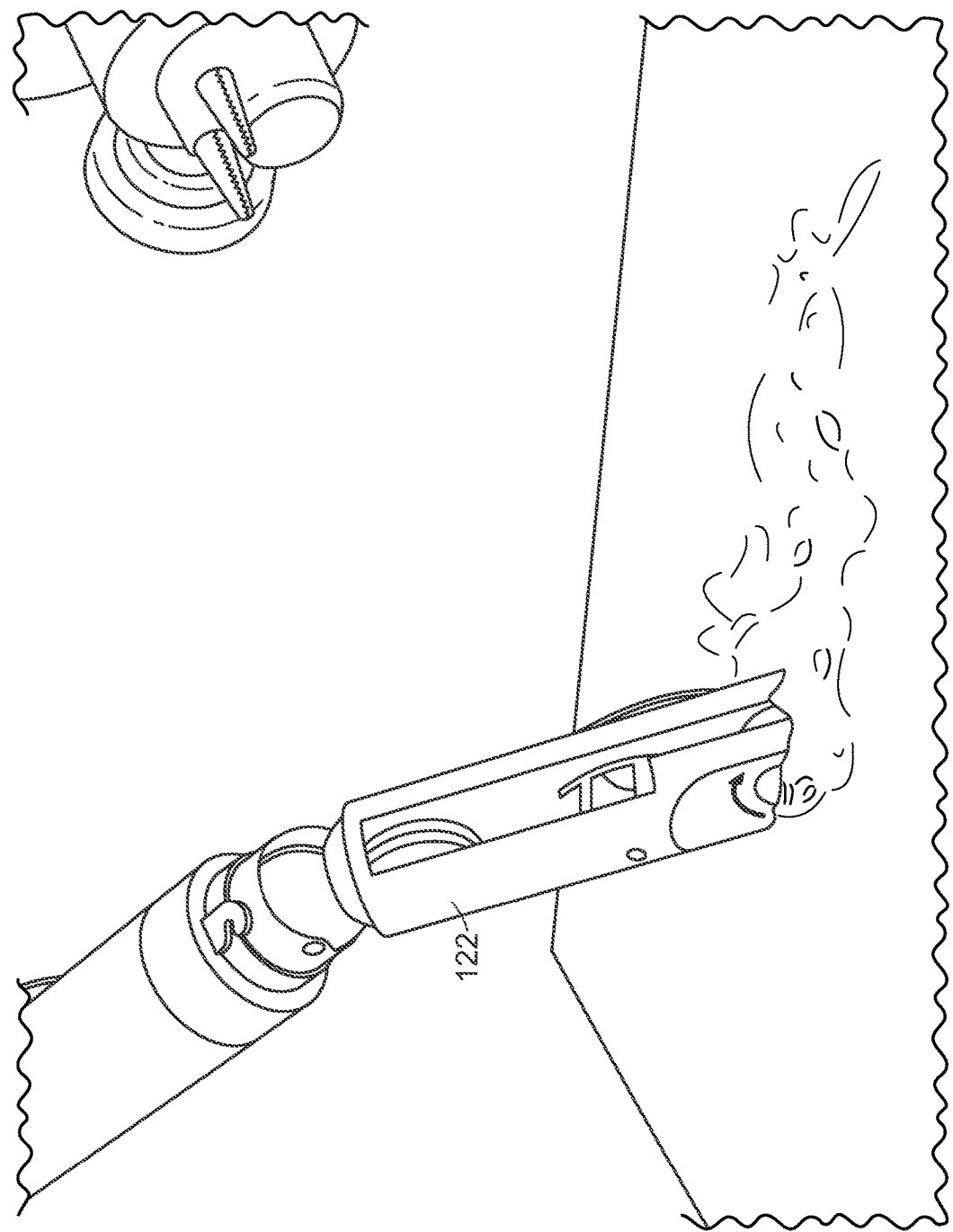

First, a stitch is thrown at a predetermined target location using the suturing end effector 122 as shown in FIGS. 10-11. The suturing end effector 122 is articulated (rotated and translated) to contact the tissue at a predetermined suture start point. A stitch is thrown at the target location by firing the suturing end effector 122 twice.

Figure 12:
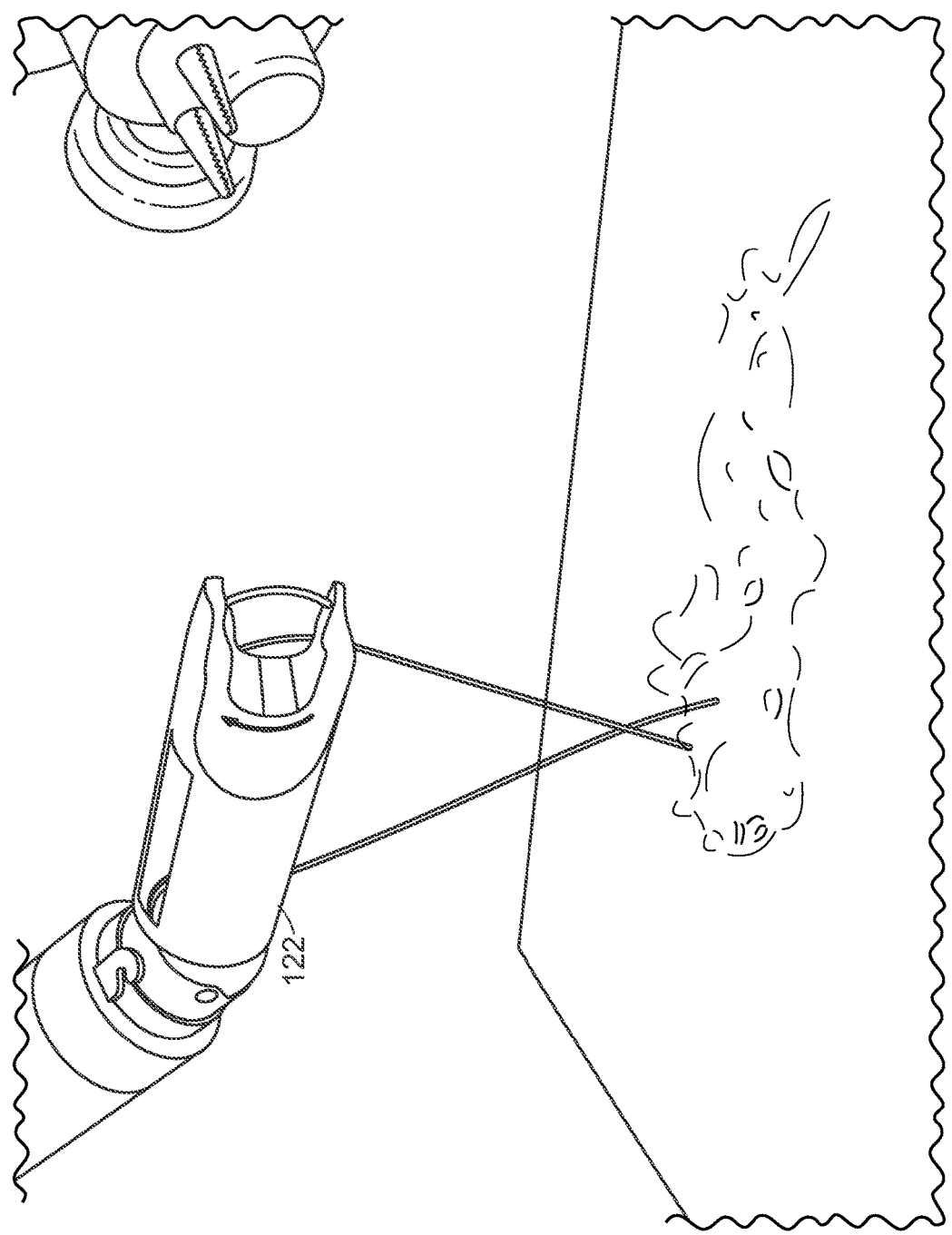

As shown in FIG. 12, the suturing end effector 122 is then retracted and articulated in an opposite direction to a home position, and the suturing end effector 122 is fired.

Figure 13:
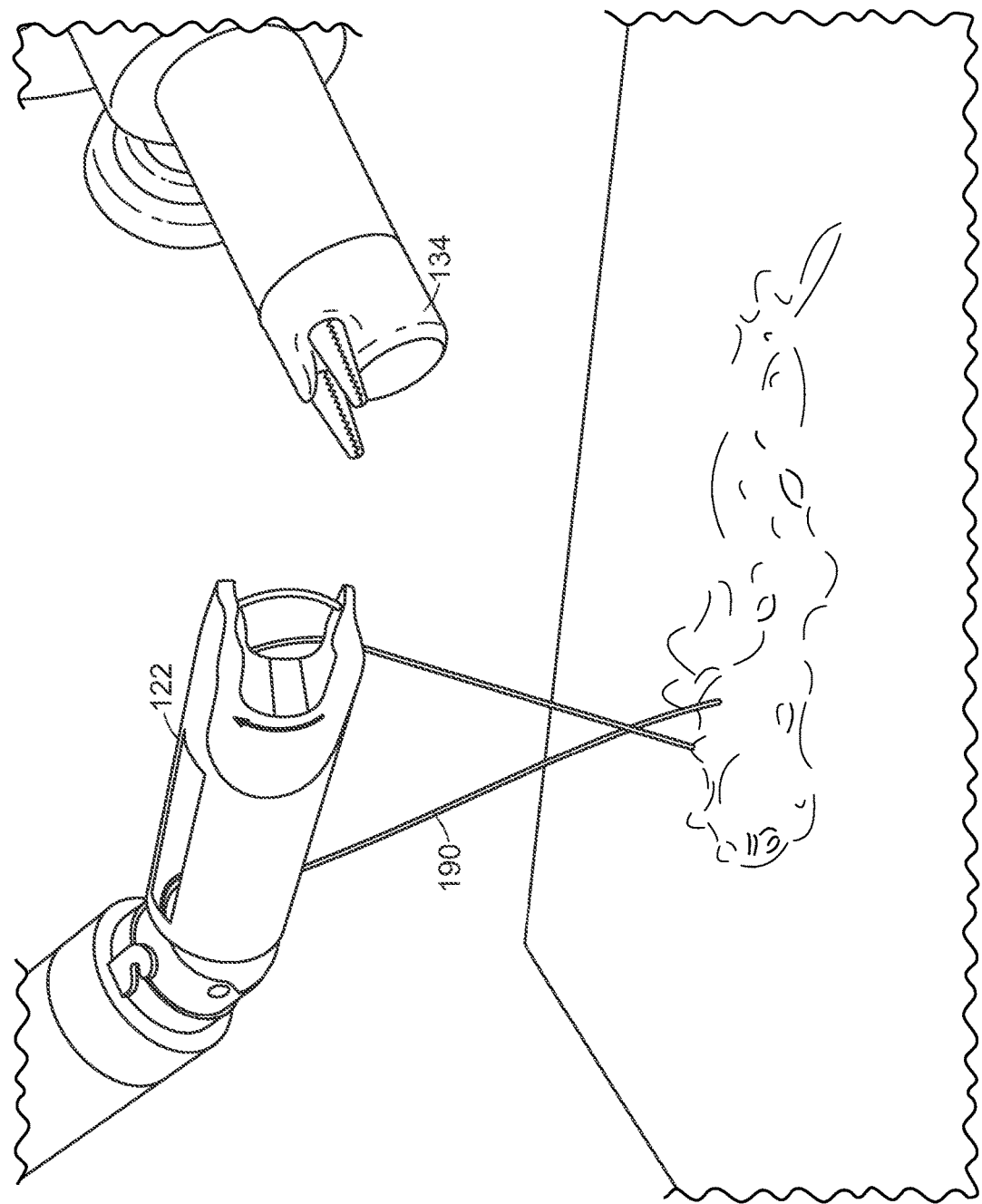
Figure 14:
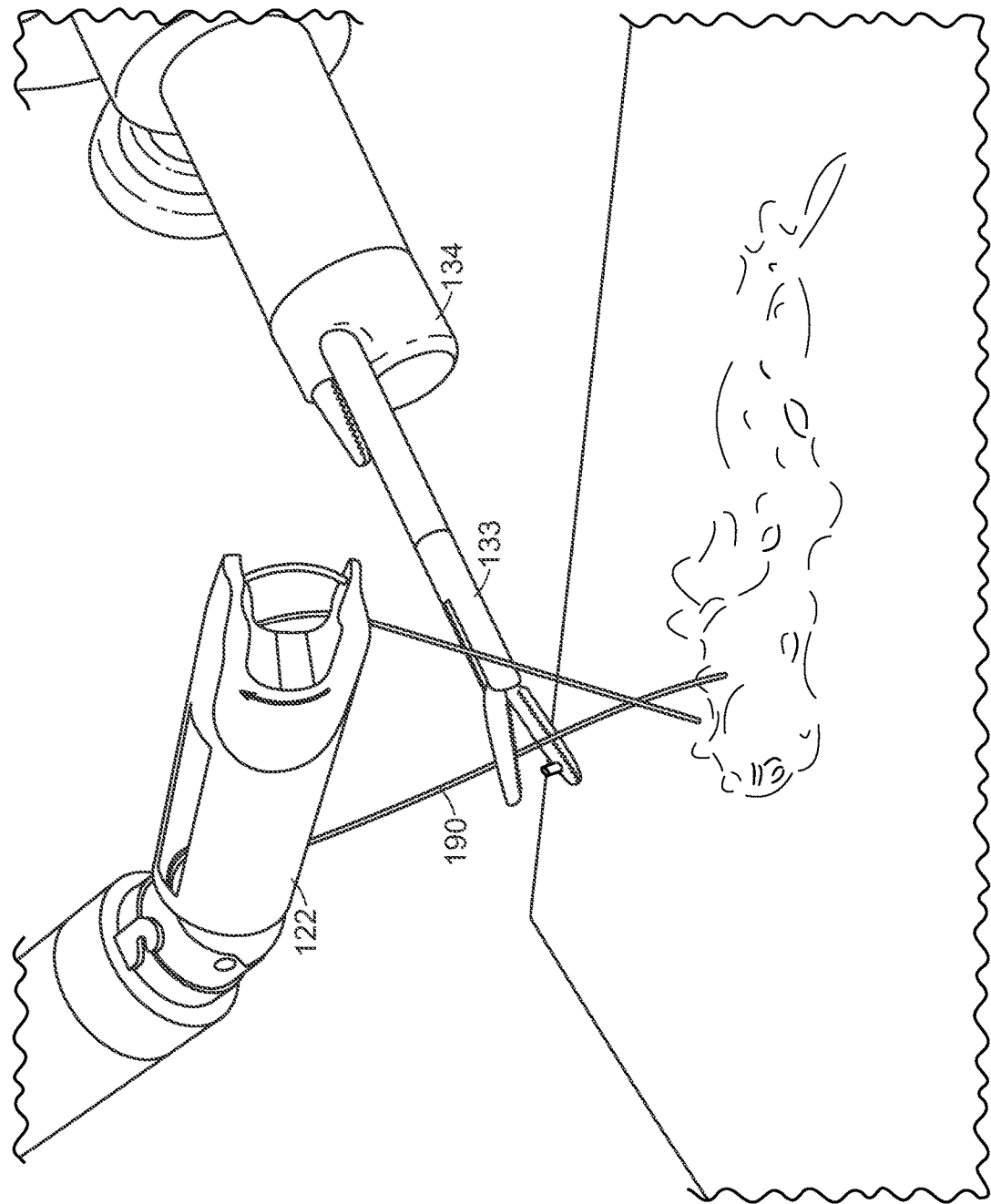

Next, as depicted in FIGS. 13 and 14, the proximal suture line 190 is secured. The camera assembly 134 is moved to aim 10° behind the suture line and 15 mm above the suture point with the camera 50 mm away (camera assembly home position). As shown in FIG. 14, grasper 133 is extended 50 mm to encapsulate the suture line 190. The grasper 133 jaws are opened before reaching the suture line 190. The grasper 133 is then closed to a suture pulley mode around the suture 190, and retracted 10 mm.

Figure 15:
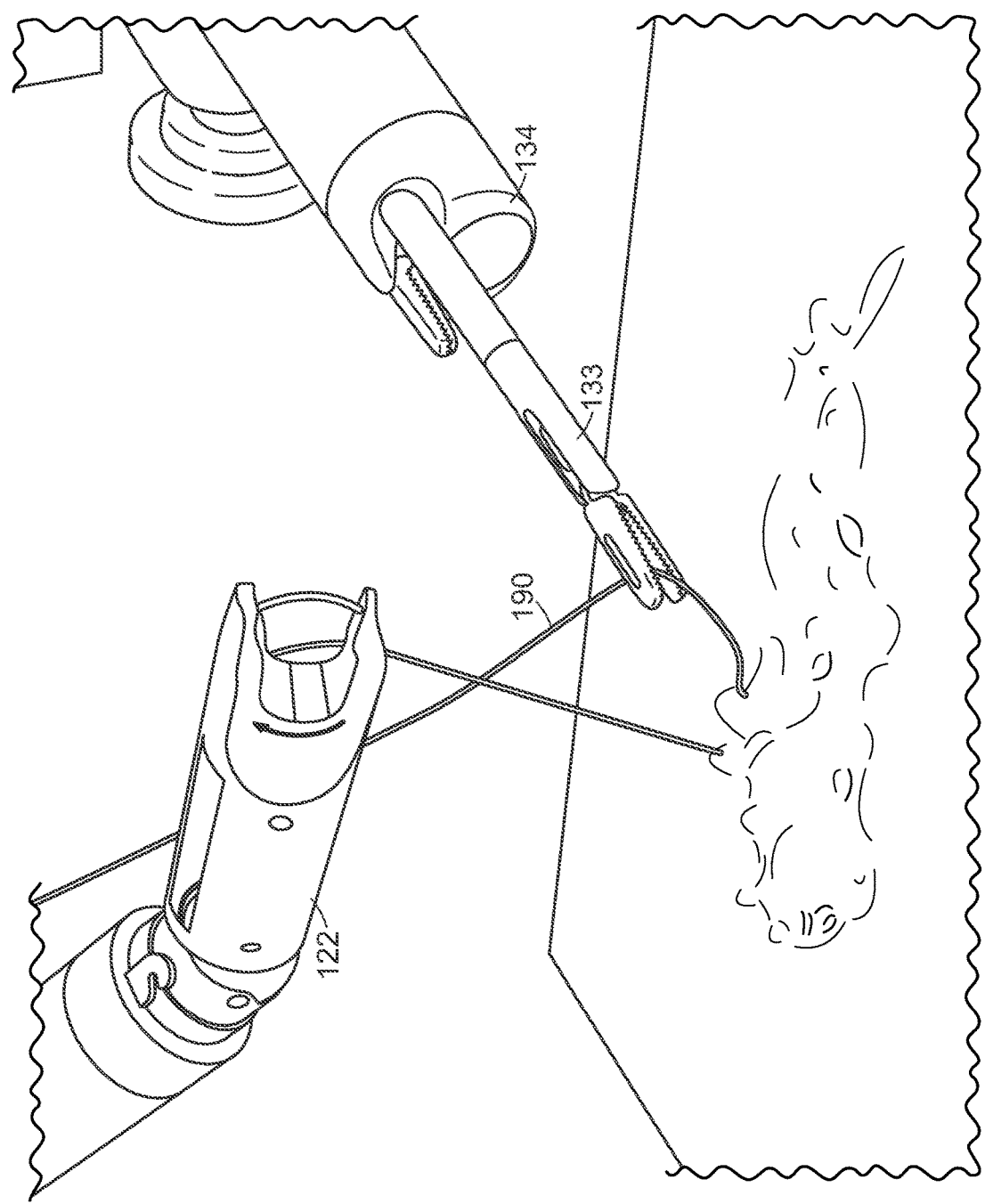
Figure 16:
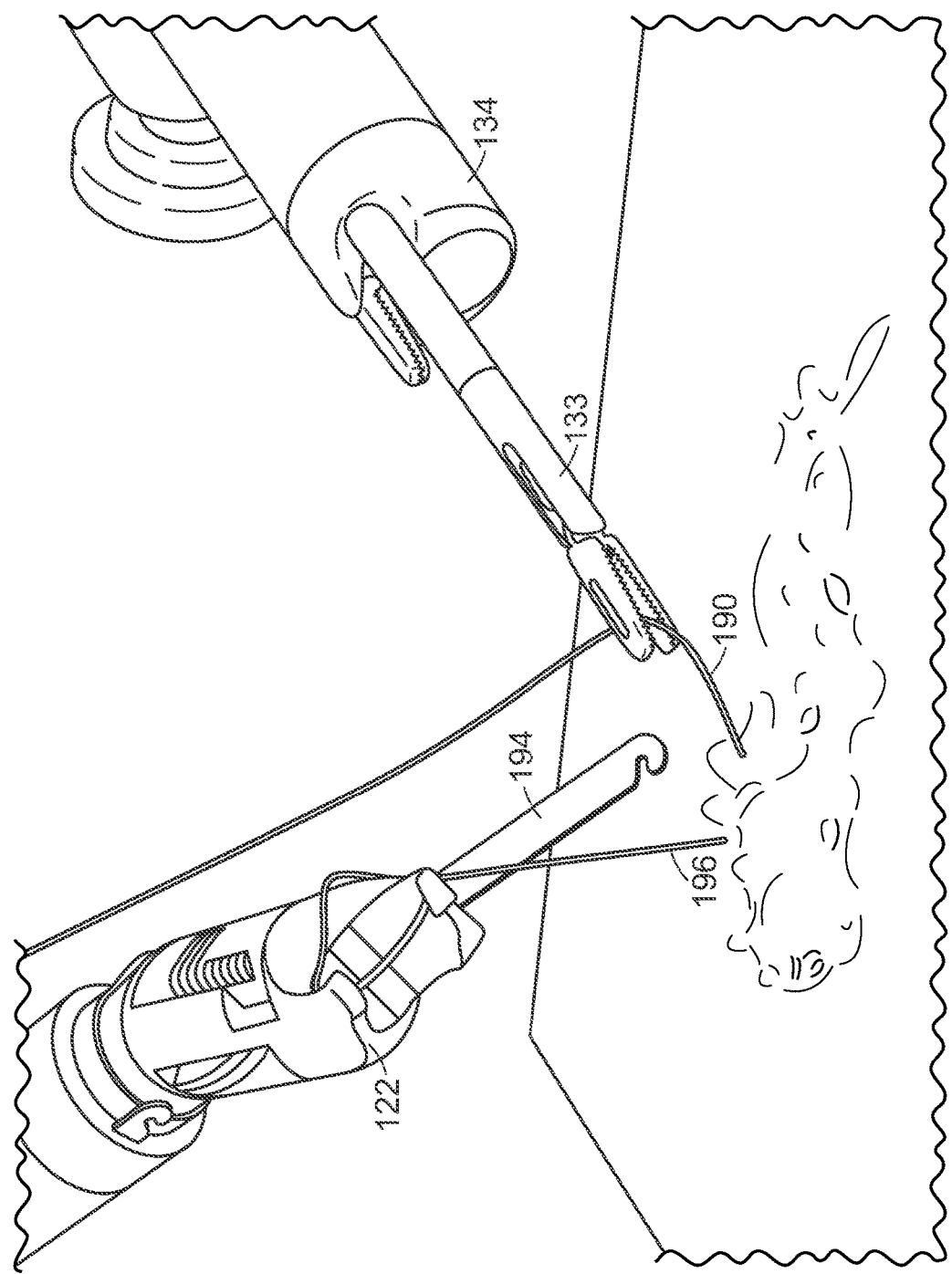
Figure 17:
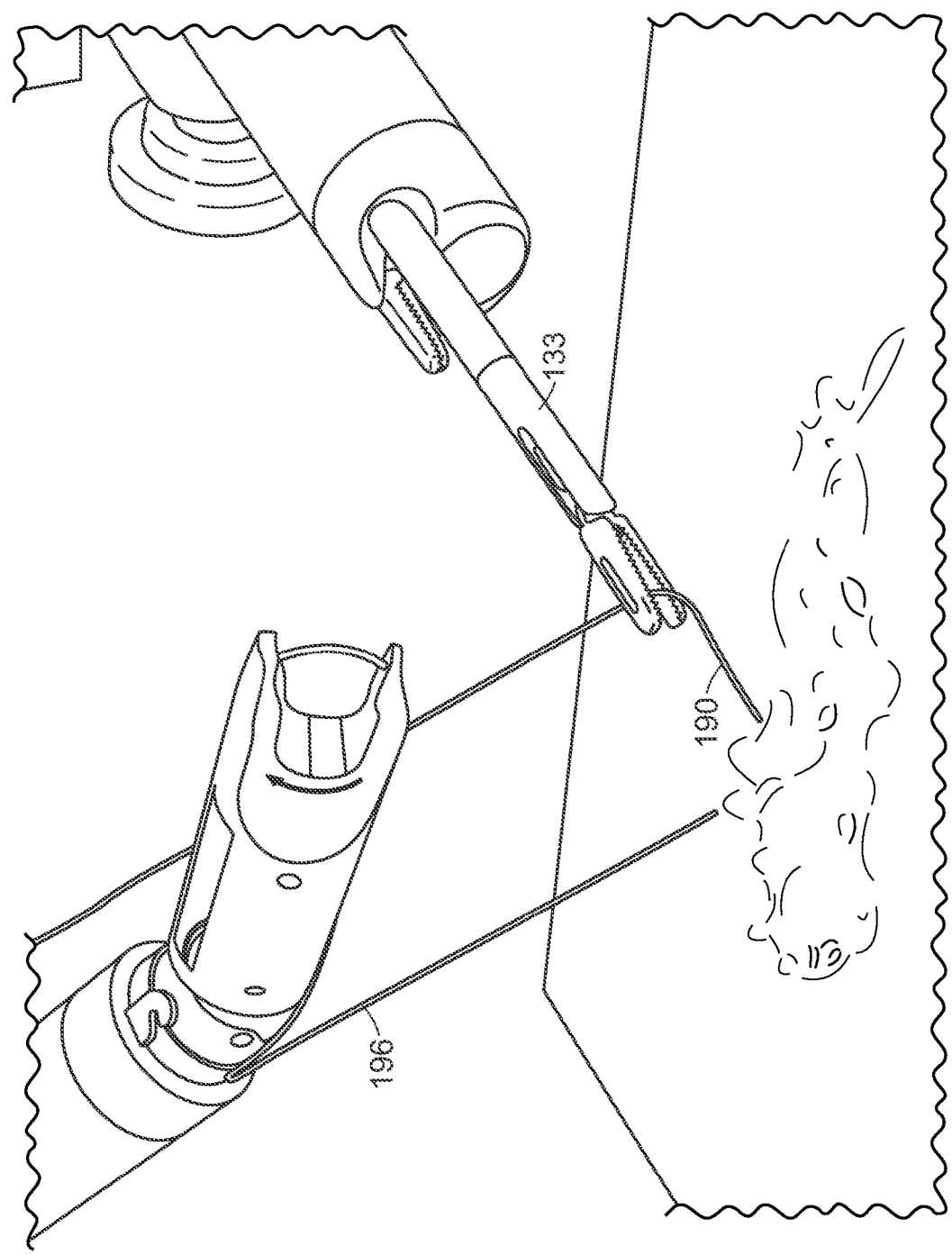

The grasper 133 is rotated −30° about the y-axis (camera assembly in a tie position), and the grasper 133 is extended 15 mm to the position shown in FIG. 15. The suturing end effector 122 is rotated 45° about the Z axis, and a hook 194 in the suturing end effector 122 is extended as shown in FIG. 16 to engage the suture line 196. The suturing end effector 122 is returned to its home position, and the hook 194 is retracted 280 mm. It locks the suture line 196 within the suturing end effector assembly 122 (FIG. 17).

Figure 18:
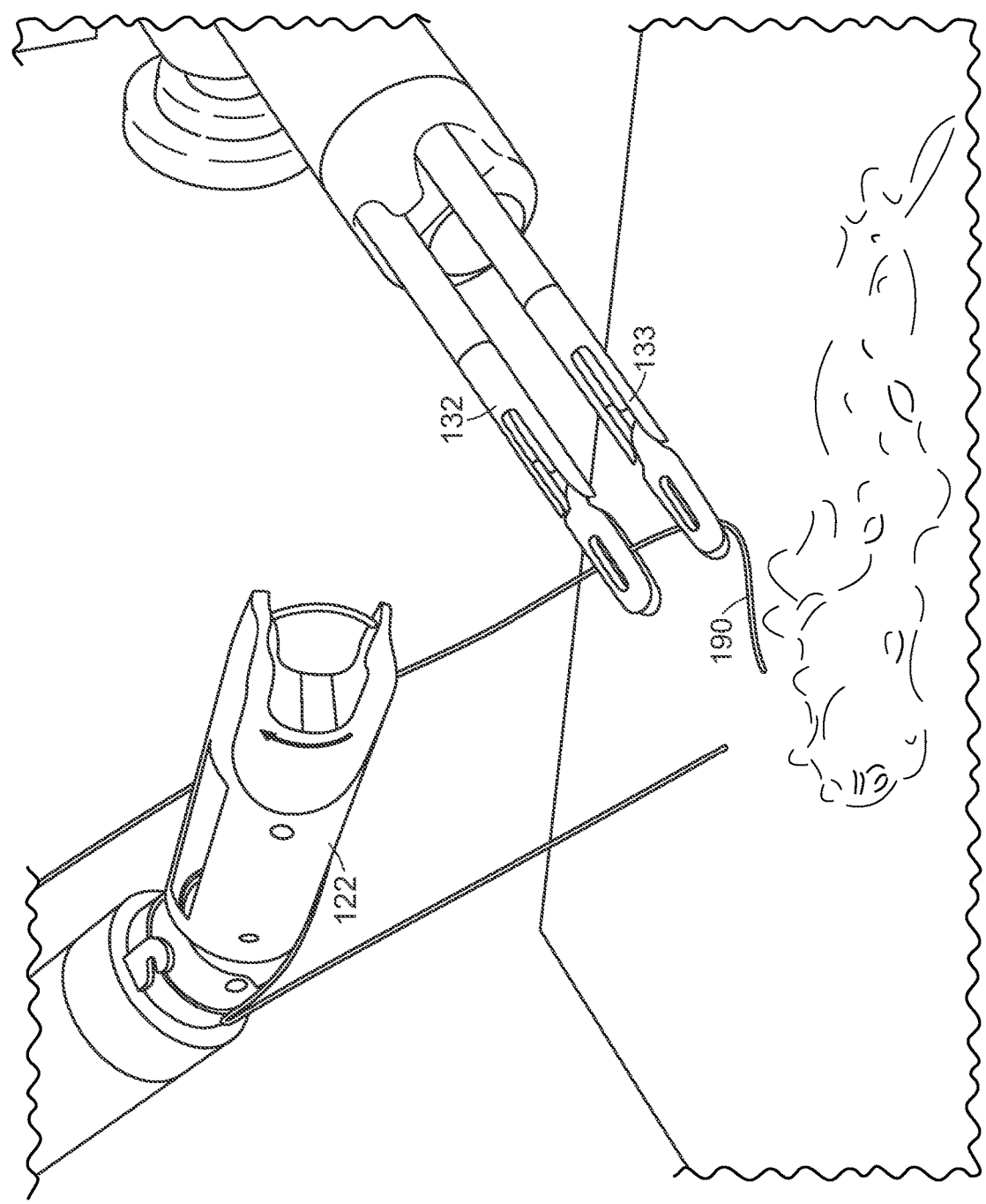

The camera assembly 134 is then rotated 45°, and the grasper 132 is extended 55 mm past the camera. The jaws of the grasper 132 are opened while it is extended. The instrument is oriented so that the hook is at the bottom. Grasper 132 is closed around the suture line 190 in a suture pulley mode as shown in FIG. 18.

Figure 19:
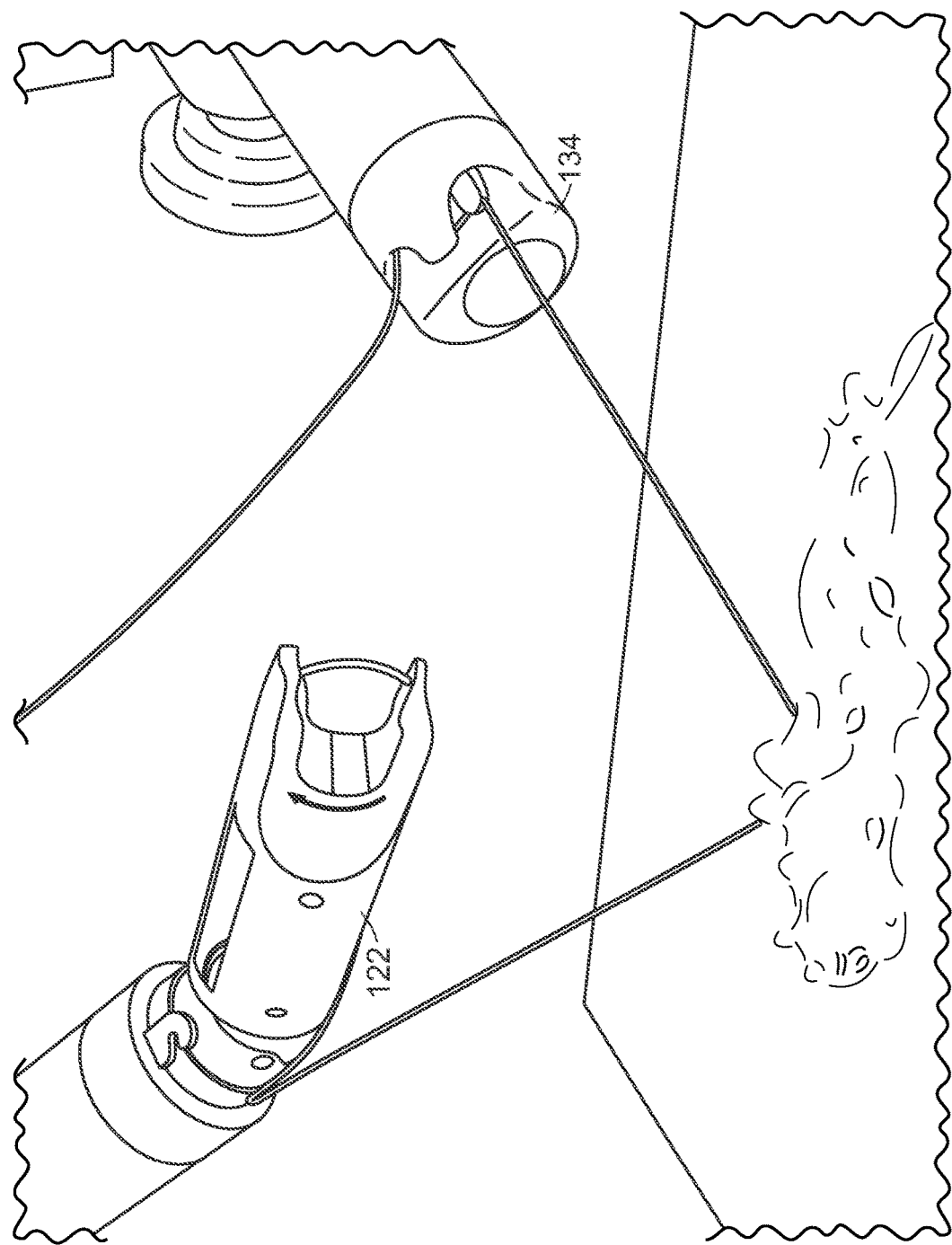

The graspers 132, 133 are retracted 55 mm to a home position in order to cut and remove the extra suture line (FIG. 19).

Figure 20:
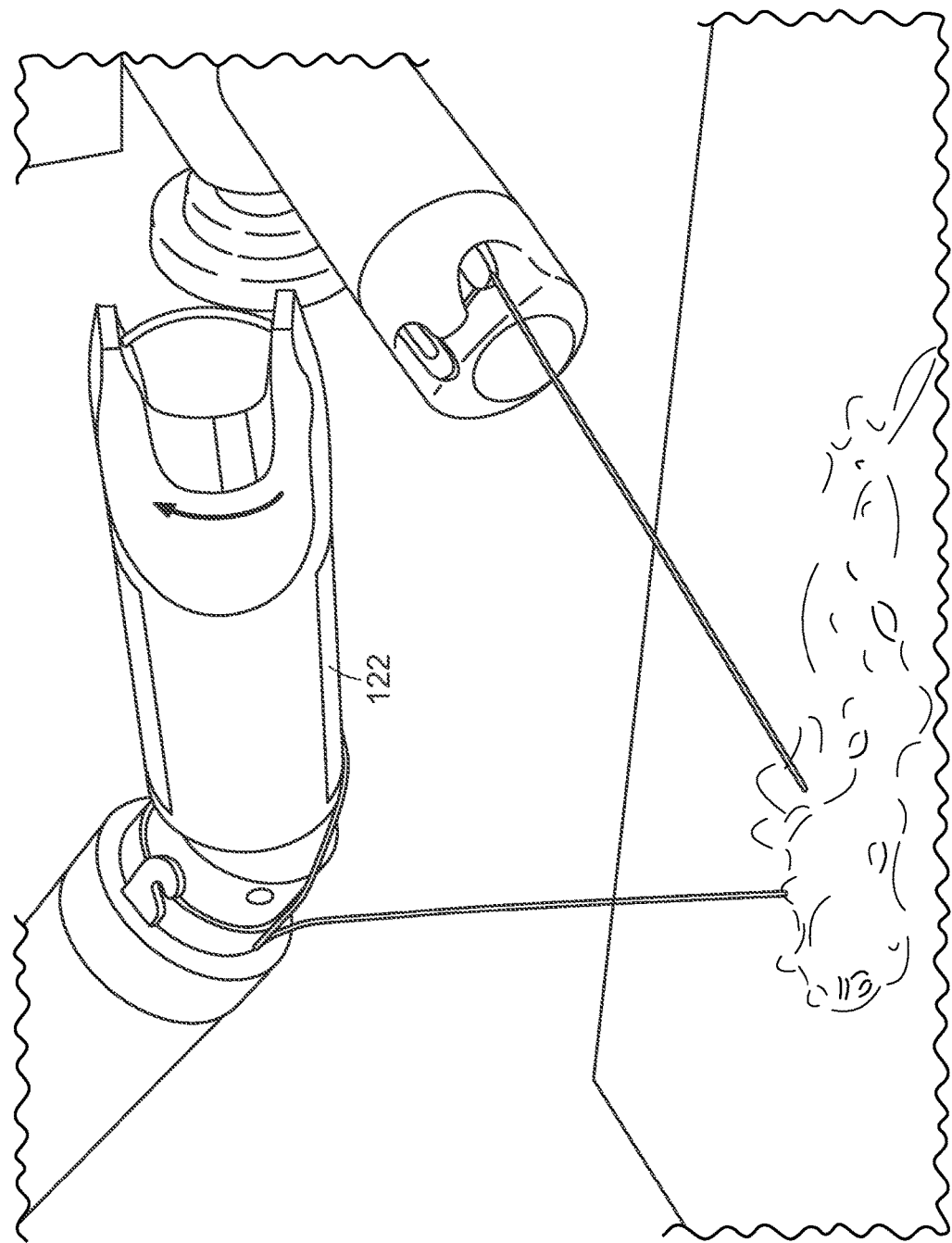

The suturing end effector 122 is extended 25 mm in order to reposition the proximal suture line. It is also rotated 10° about the X axis. This orients the proximal suture line for knot tying as shown in FIG. 20.

Figure 21:
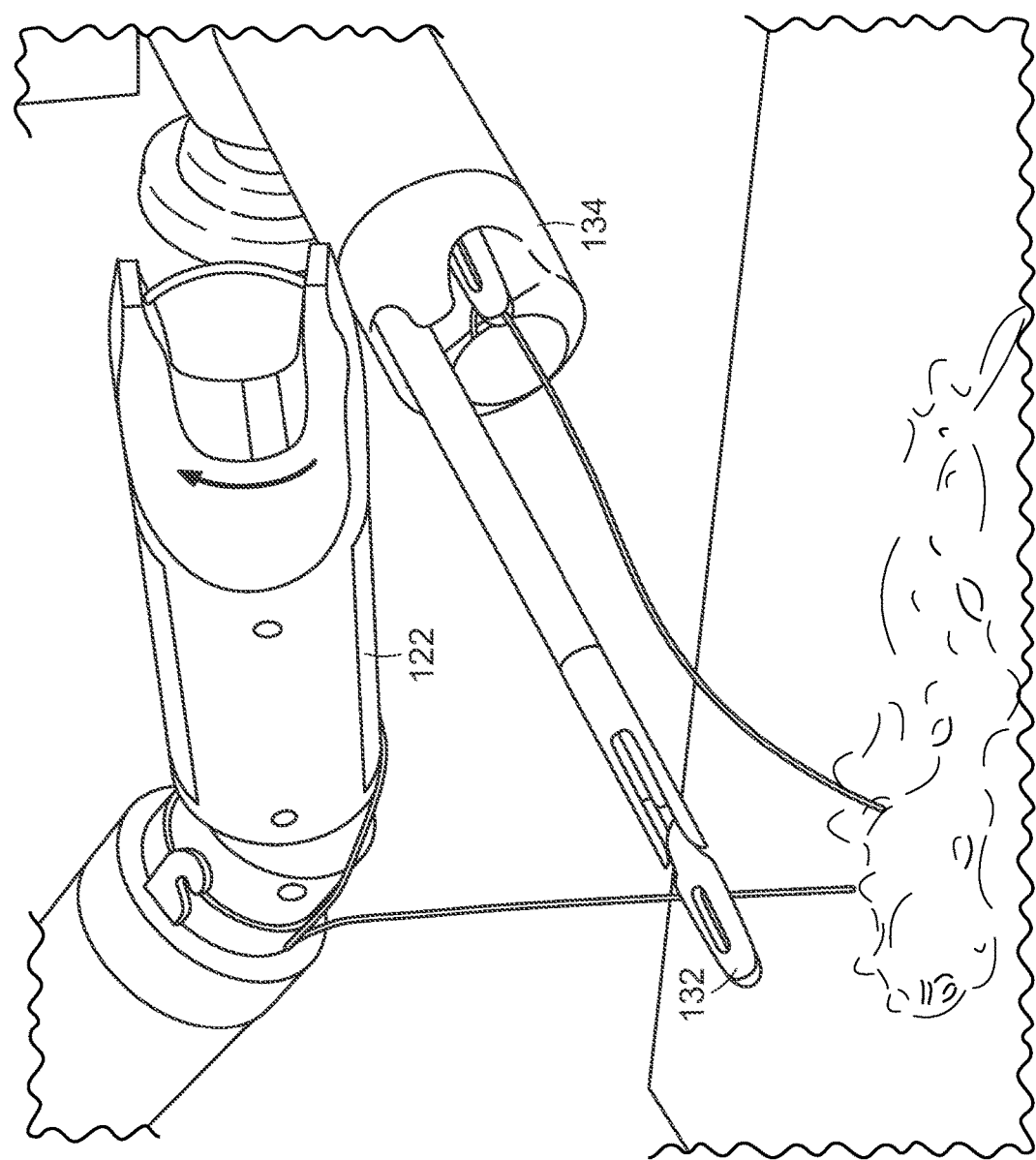

Next, the first loop of the square knot is created. The camera assembly 134 is rotated 5° on the Y axis. The grasper 132 is extended 55 mm and oriented so the hook is on the bottom as shown in FIG. 21.

Figure 22:
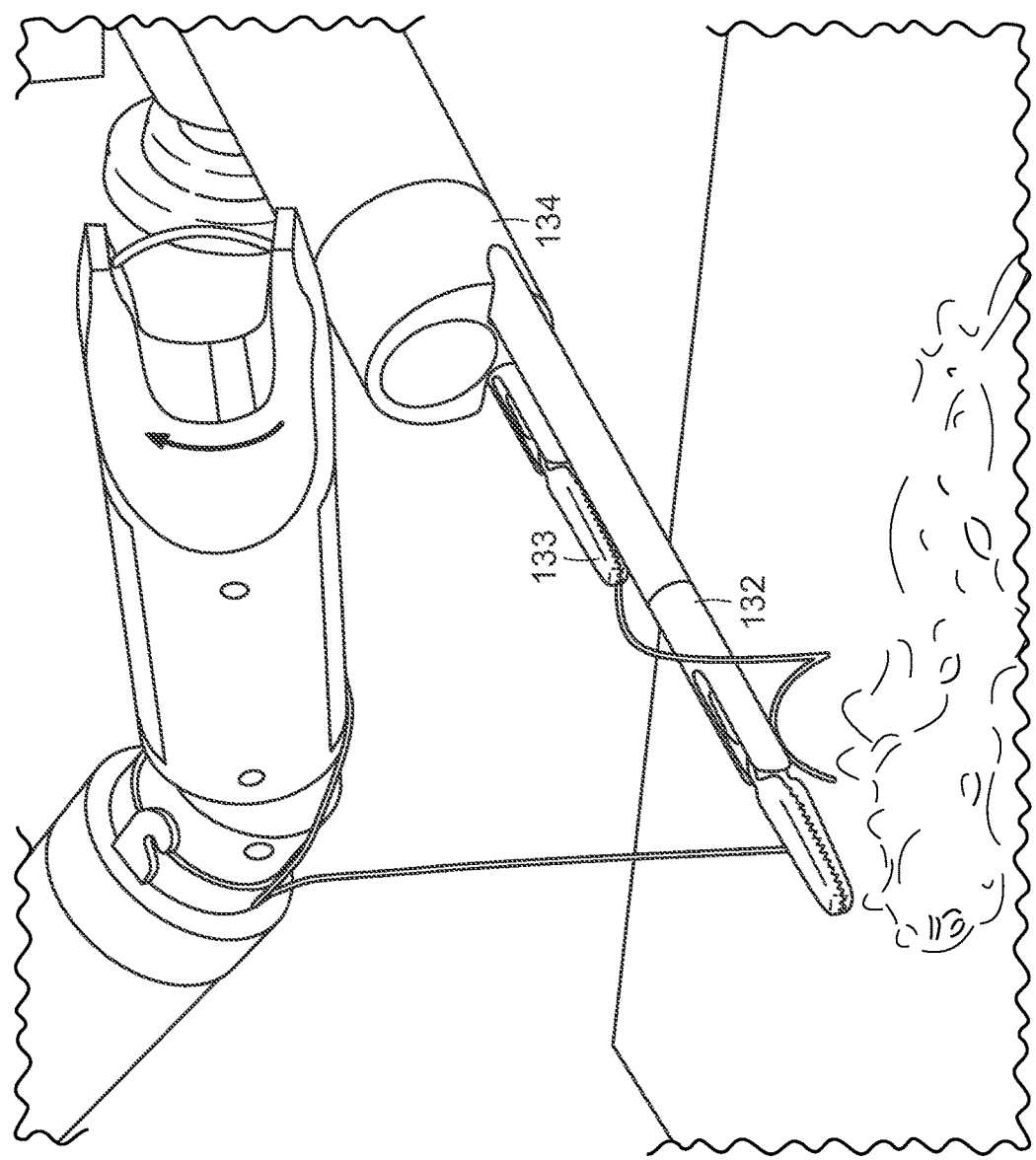

Grasper 133 is extended 25 mm, and the camera assembly 134 is rotated 180° as shown in FIG. 22.

Figure 23:
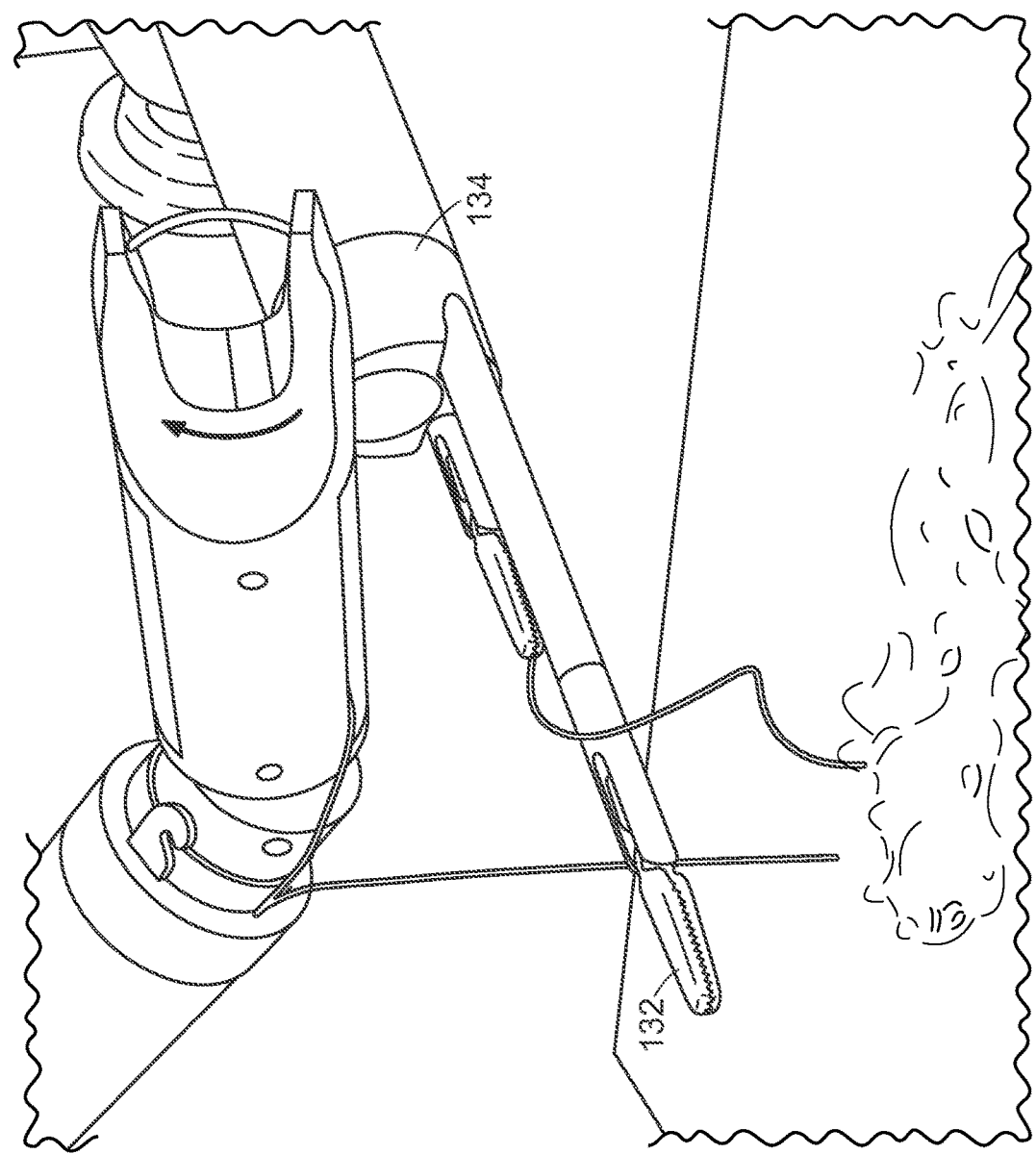
Figure 24:
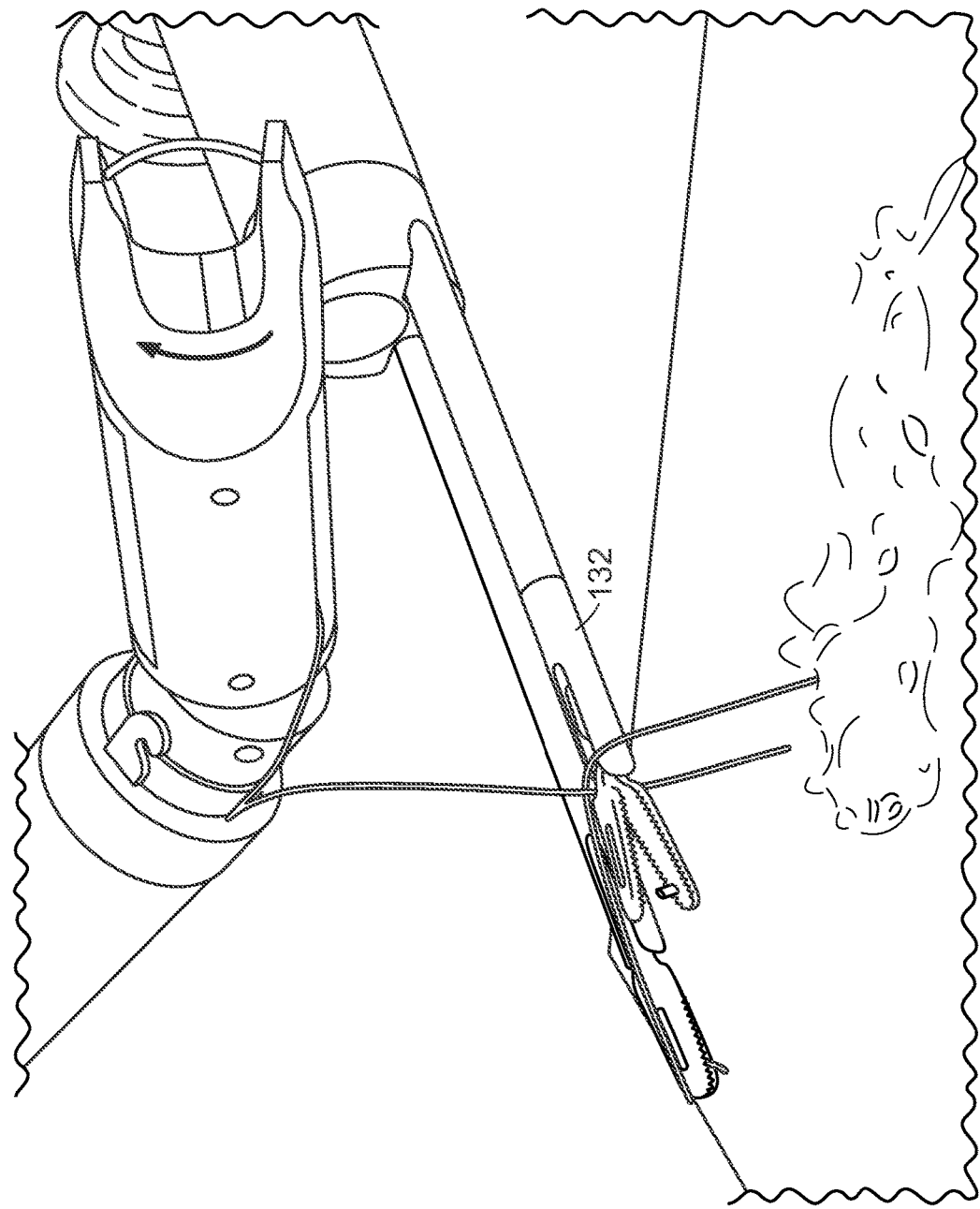

The camera assembly 134 is rotated 30° on the y-axis as shown in FIG. 23. Grasper 132 is next to the suturing end effector 122 suture line. The camera assembly 134 is in a home position.

Figure 25:
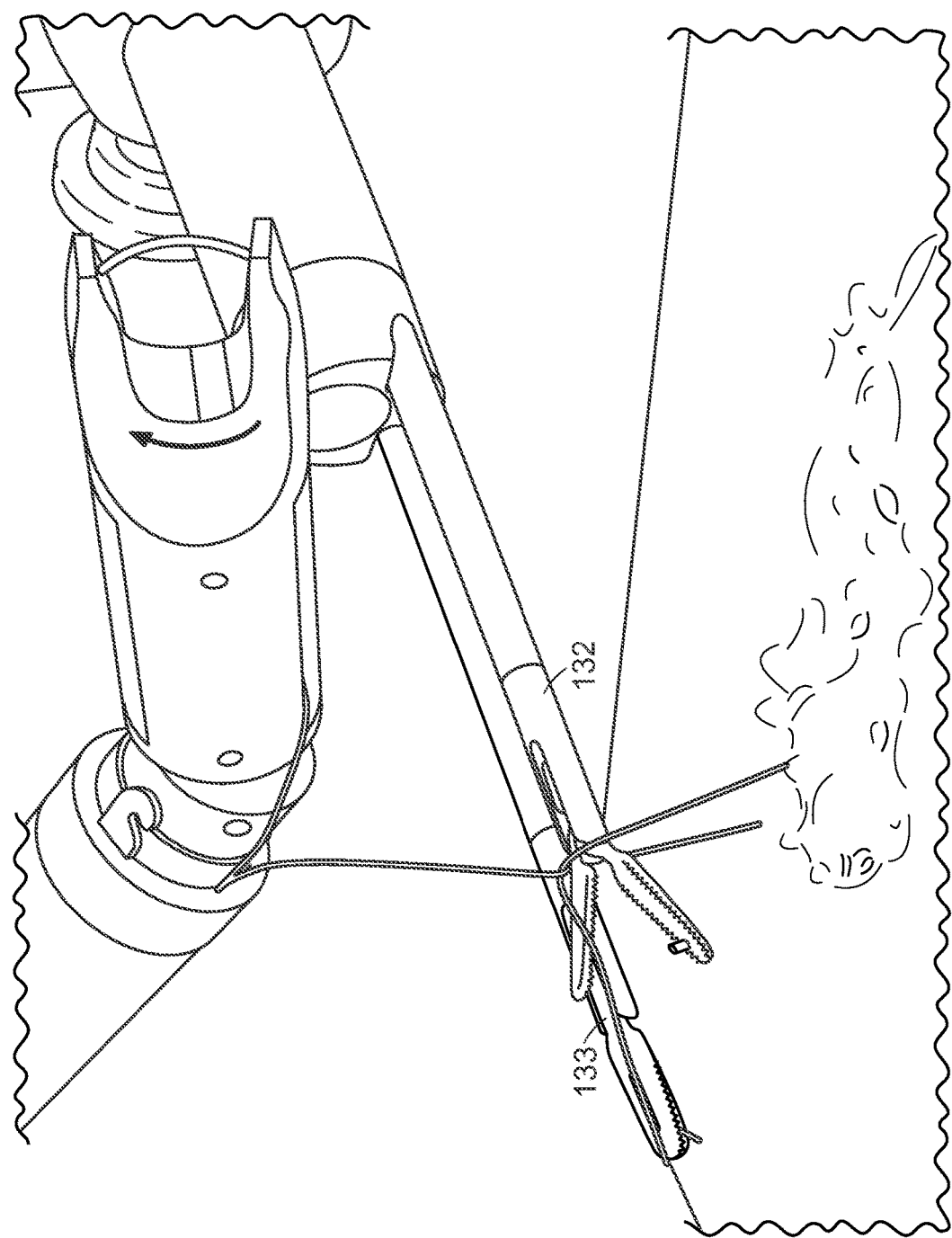

Grasper 133 is extended 60 mm (FIG. 24) and grasper 132 is opened and rotated −180° (FIG. 25).

Figure 26:
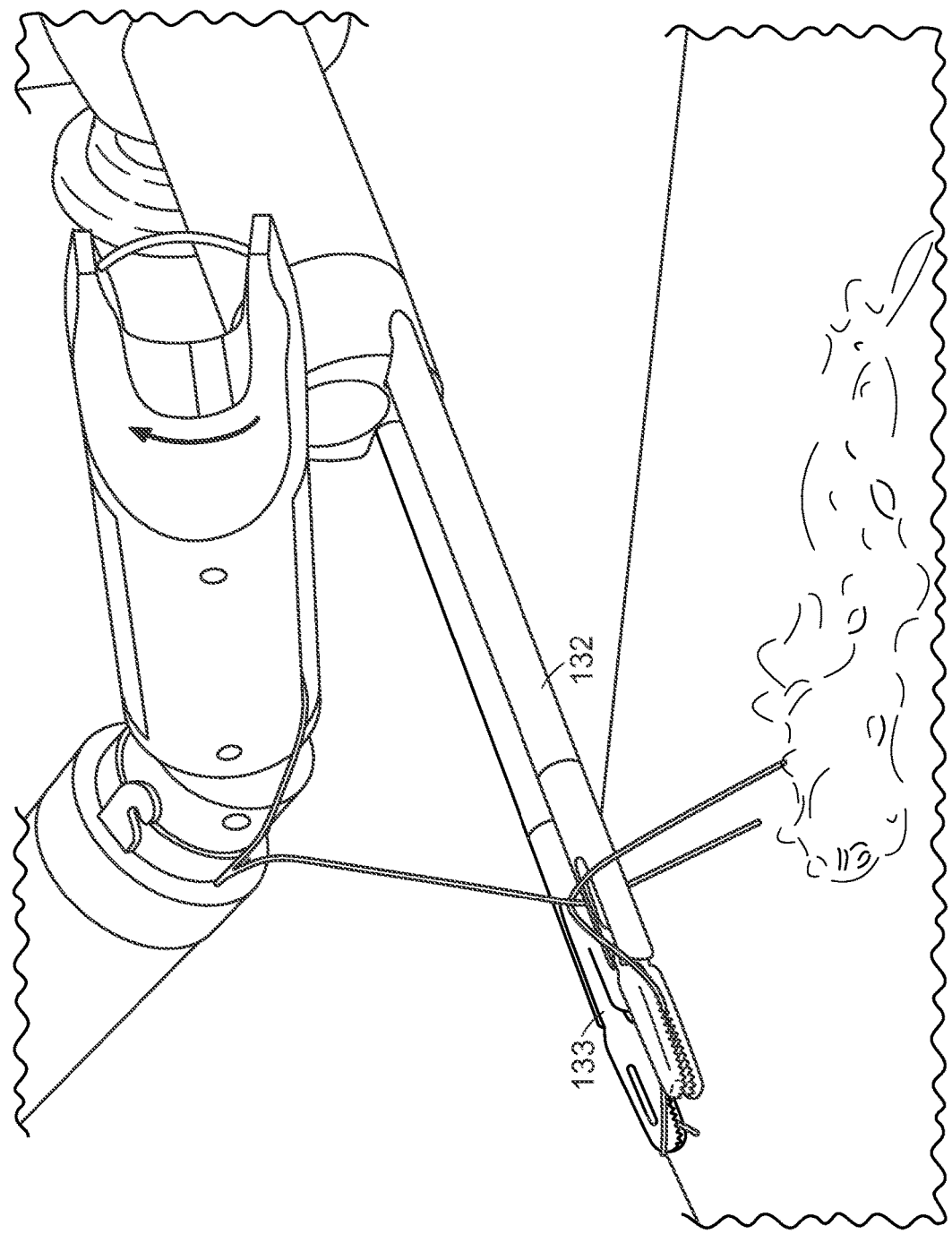

Grasper 132 is extended 5 mm, and is fully closed (FIG. 26).

Grasper 133 is fully opened and retracted.

Figure 27:
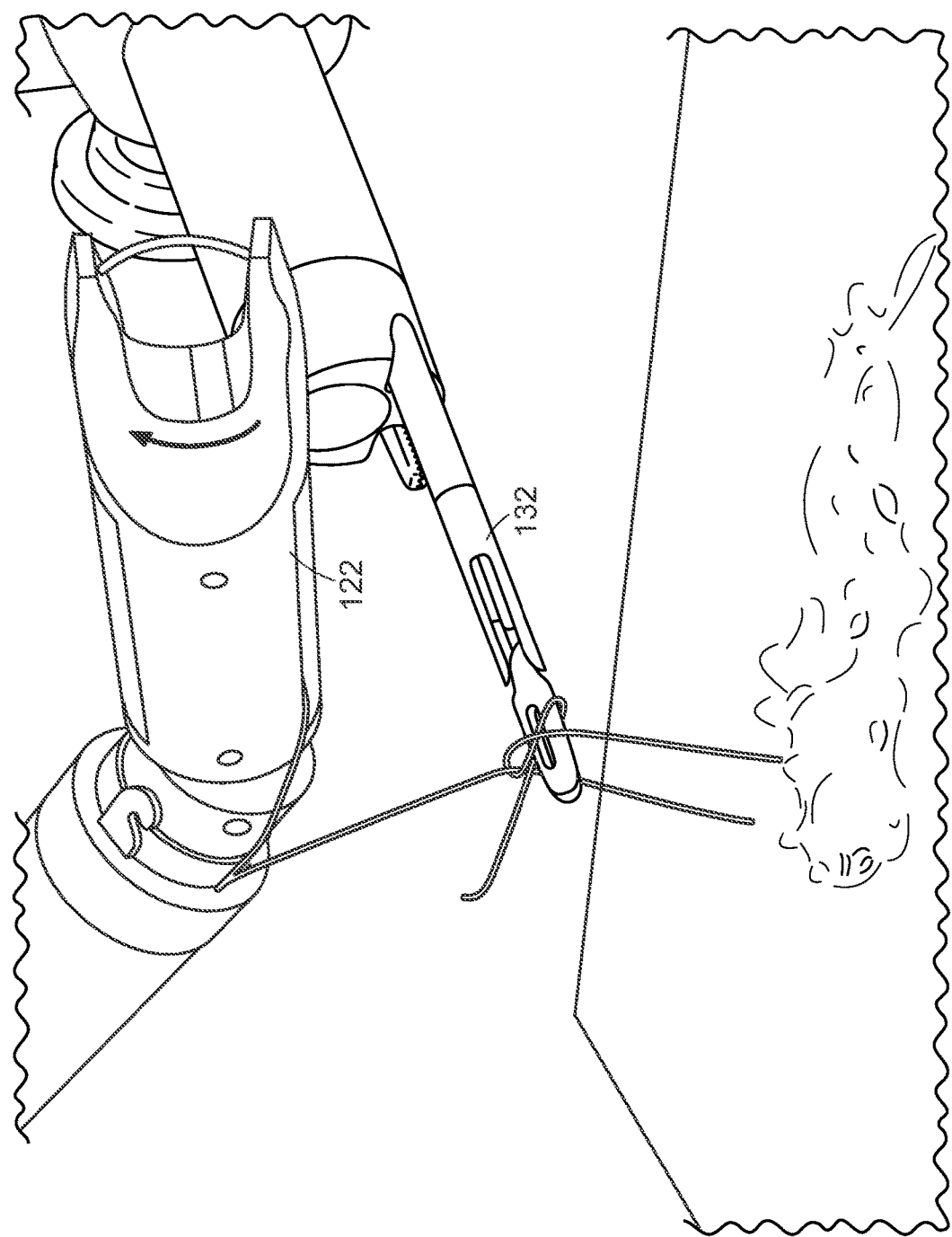

Grasper 132 is positioned 10 mm past the camera (FIG. 27).

Figure 28:
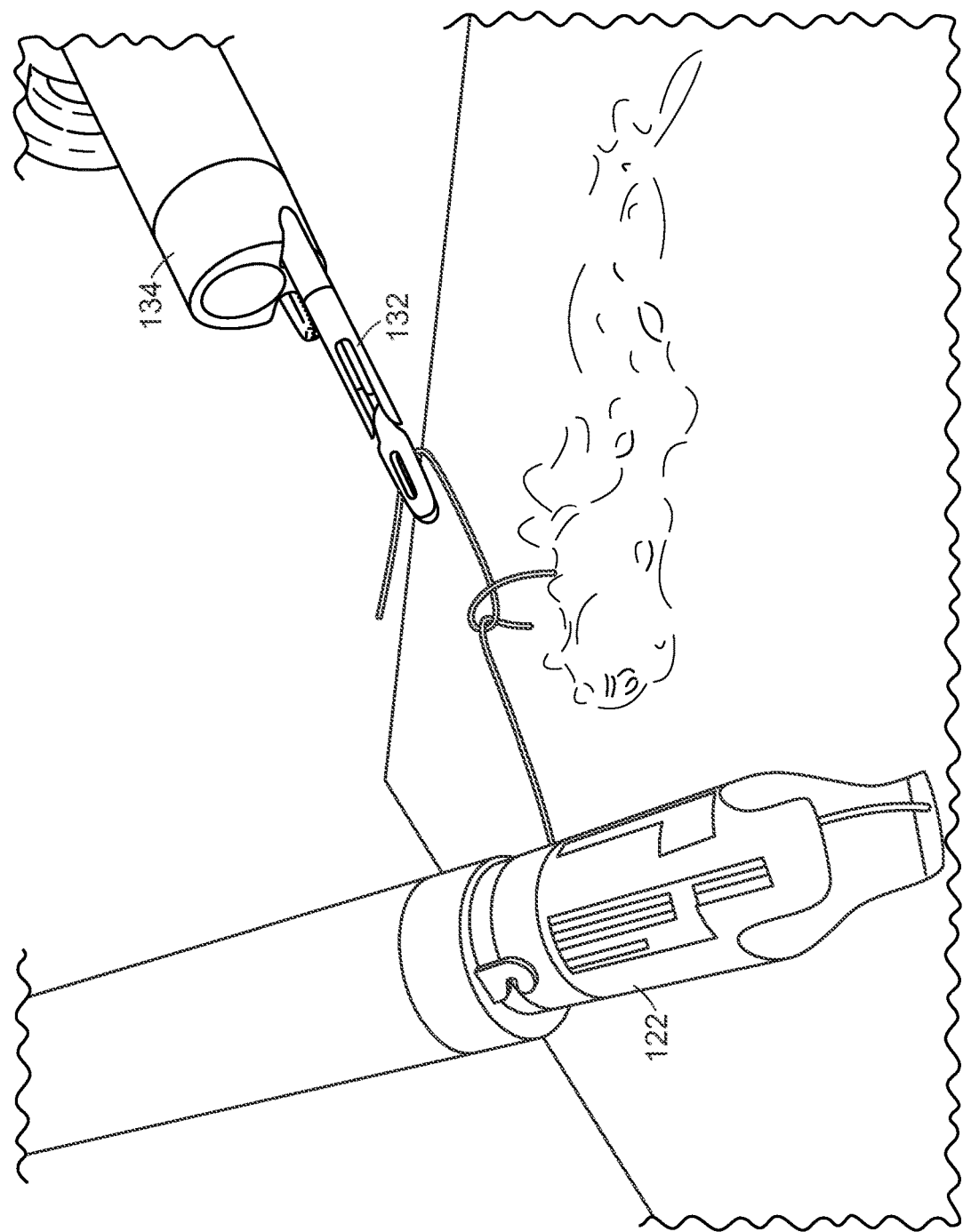

The loop is tightened onto the tissue by extending the suturing end effector 122 so that it is against the tissue and 15 mm away from the suture point. This provides a counter-traction for tying the knot (FIG. 28). The camera assembly 134 is moved to a cinch position and retracted along the surface until the suture is taught.

Figure 29:
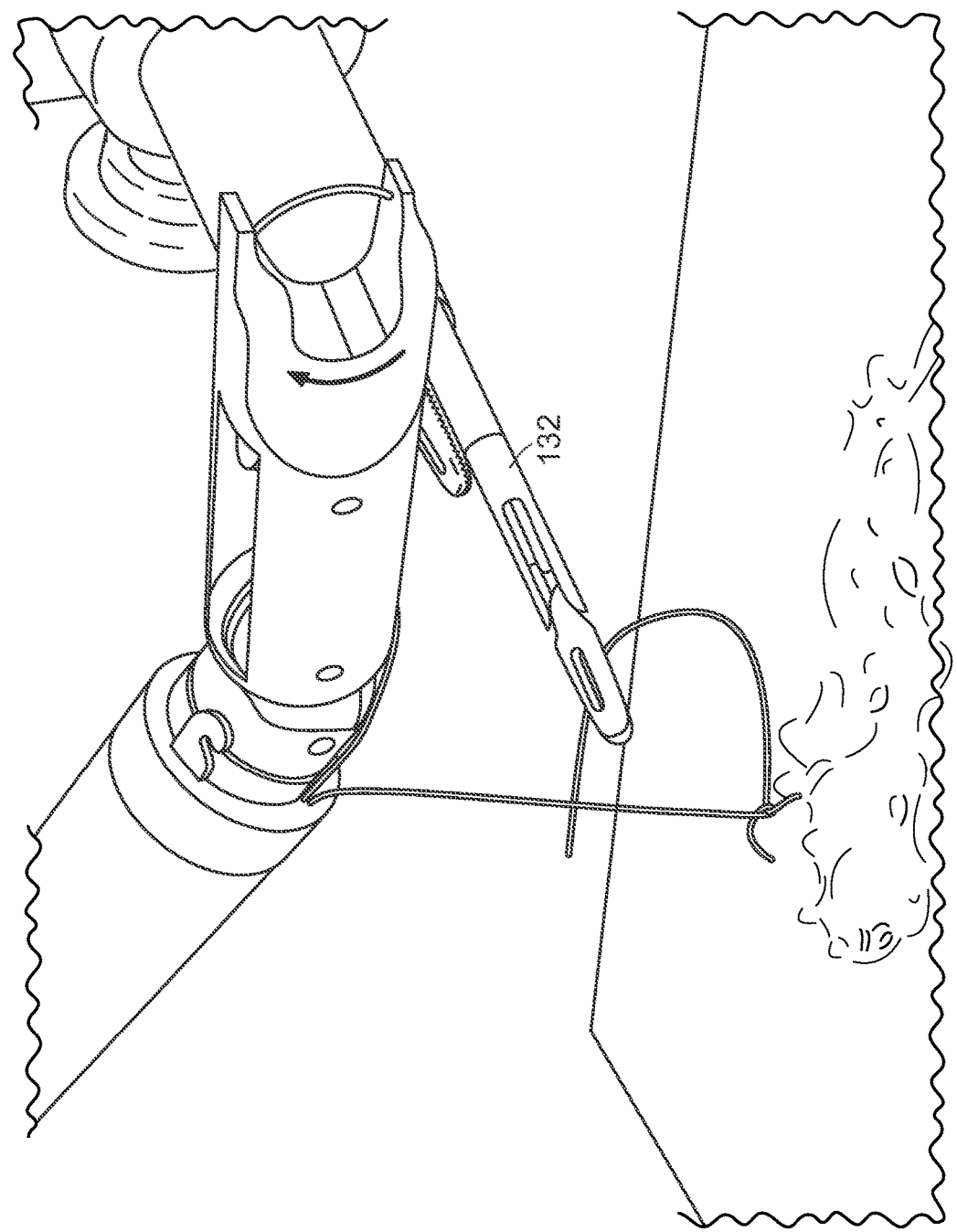

The suturing end effector 122 is then returned to a home position in order to prepare for a second loop for the square knot. The camera assembly 134 is returned to the Tie position. Grasper 132 is extended 15 mm (FIG. 29).

Figure 30:
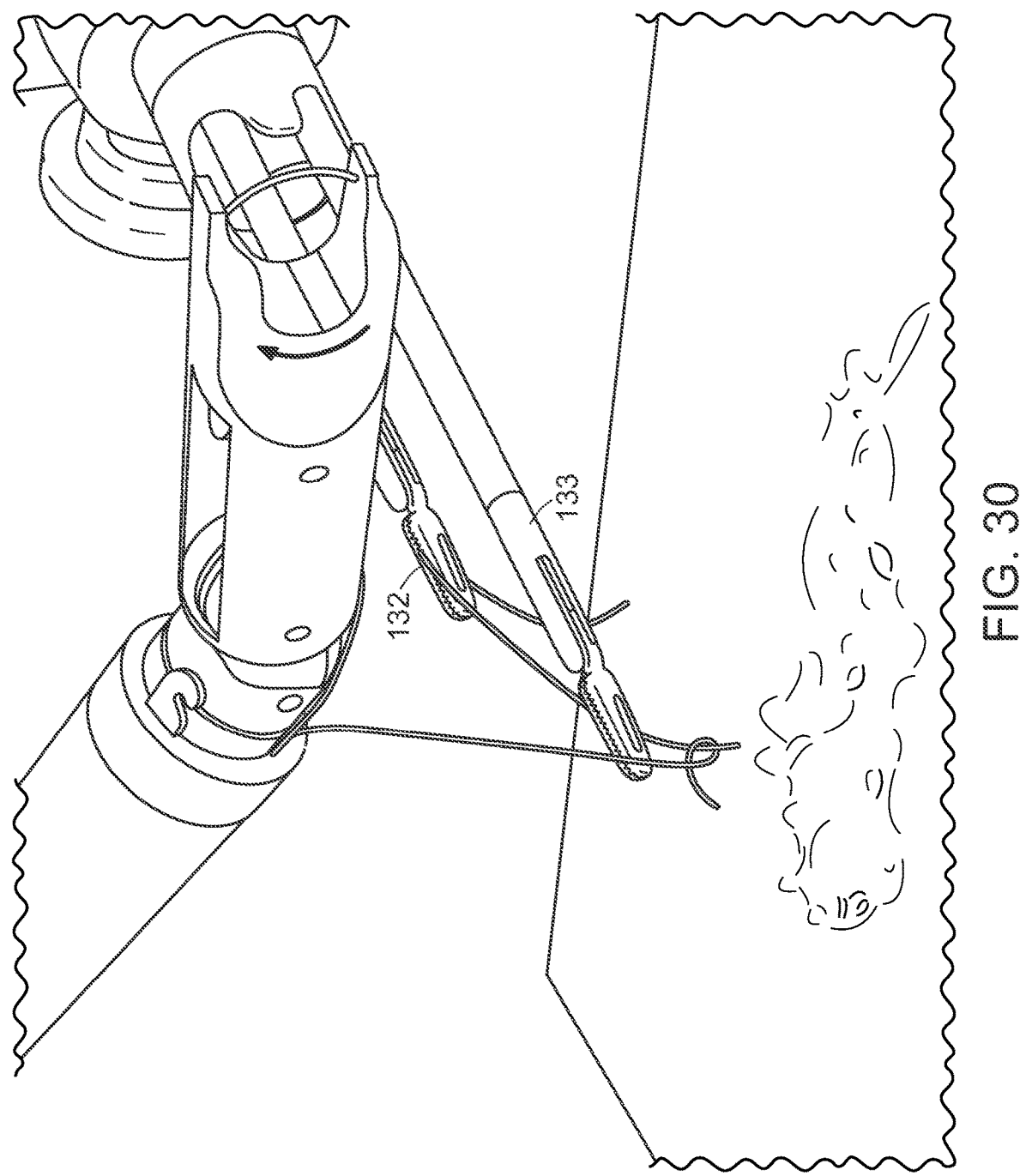

Grasper 133 is extended 50 mm and the camera assembly 134 is rotated 360° as shown in FIG. 30.

Grasper 133 is extended 15 mm, and grasper 132 is extended 40 mm.

Figure 31:
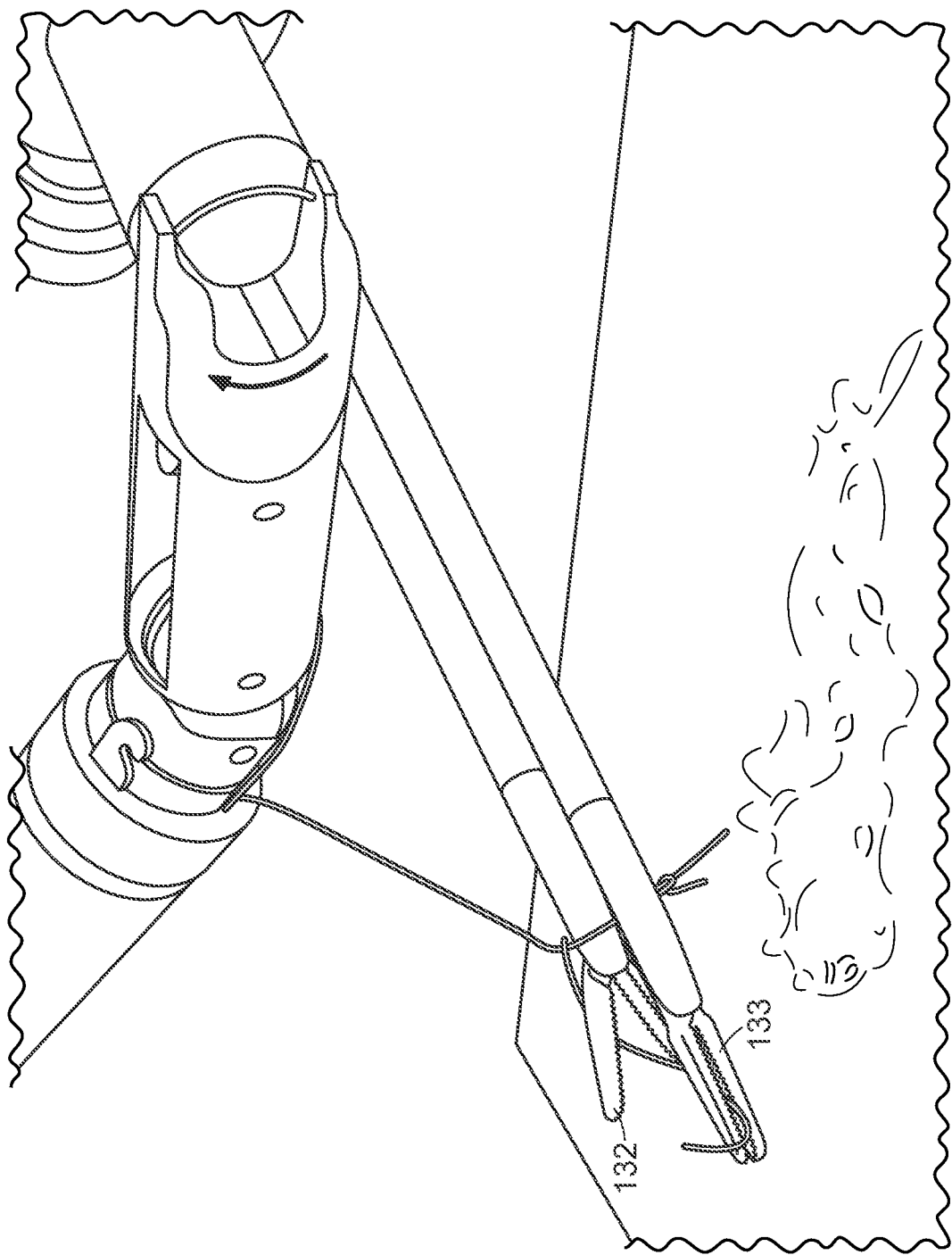

Grasper 132 is rotated 180°. Grasper 133 is fully opened and rotated 180°, and then extended 15 mm (FIG. 31).

Grasper 133 is fully closed (i.e., in a suture grasping mode).

Figure 32:
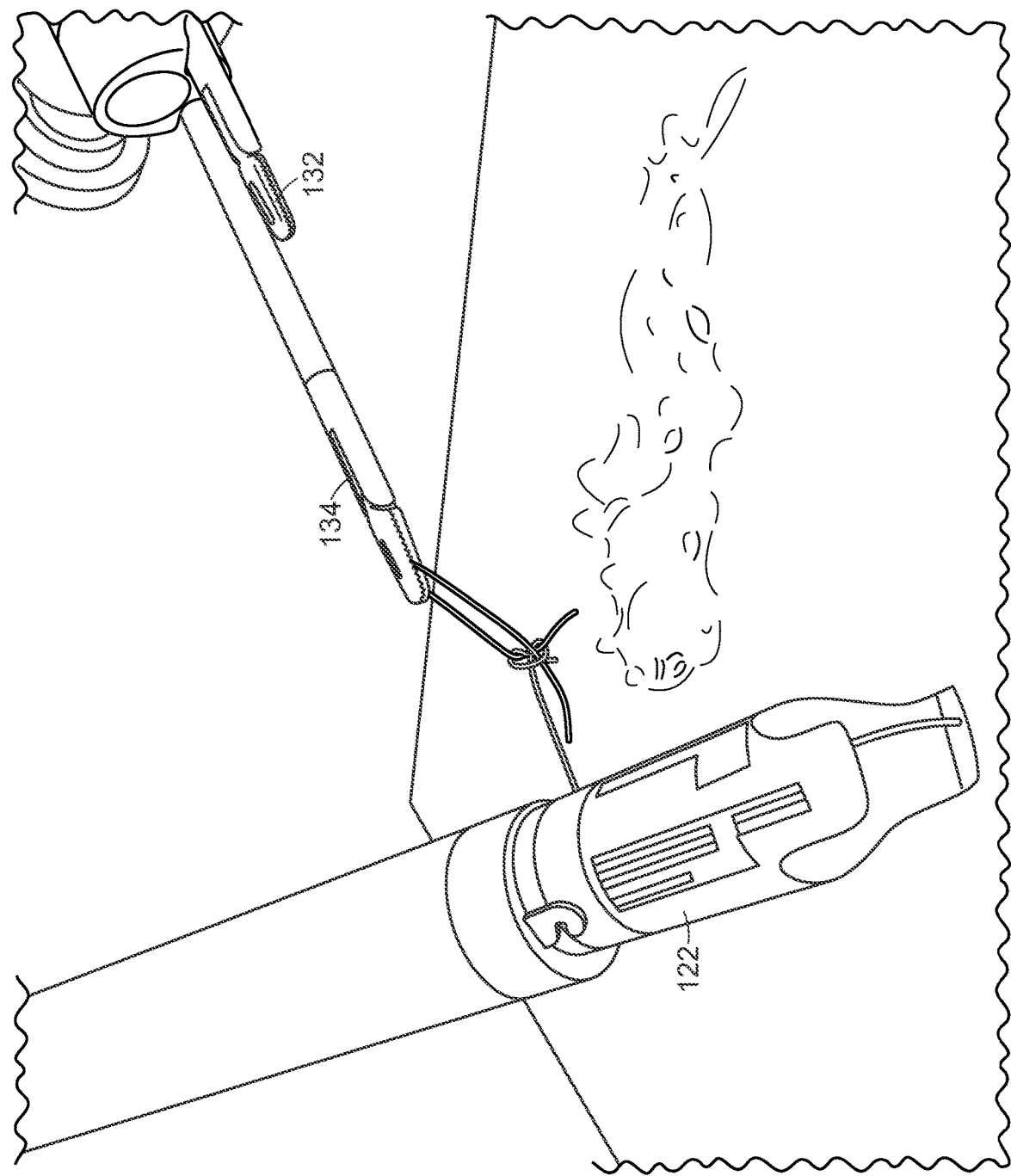

Grasper 132 is fully opened and returned to home position (FIG. 32).

Next, the square knot is tightened onto the tissue. The suturing end effector 122 is extended so that it is against tissue and 25 mm away from the suture point (FIG. 32). This provides counter-traction for tying the knot. The camera assembly 134 is retracted until the suture is taught.

Figure 33:
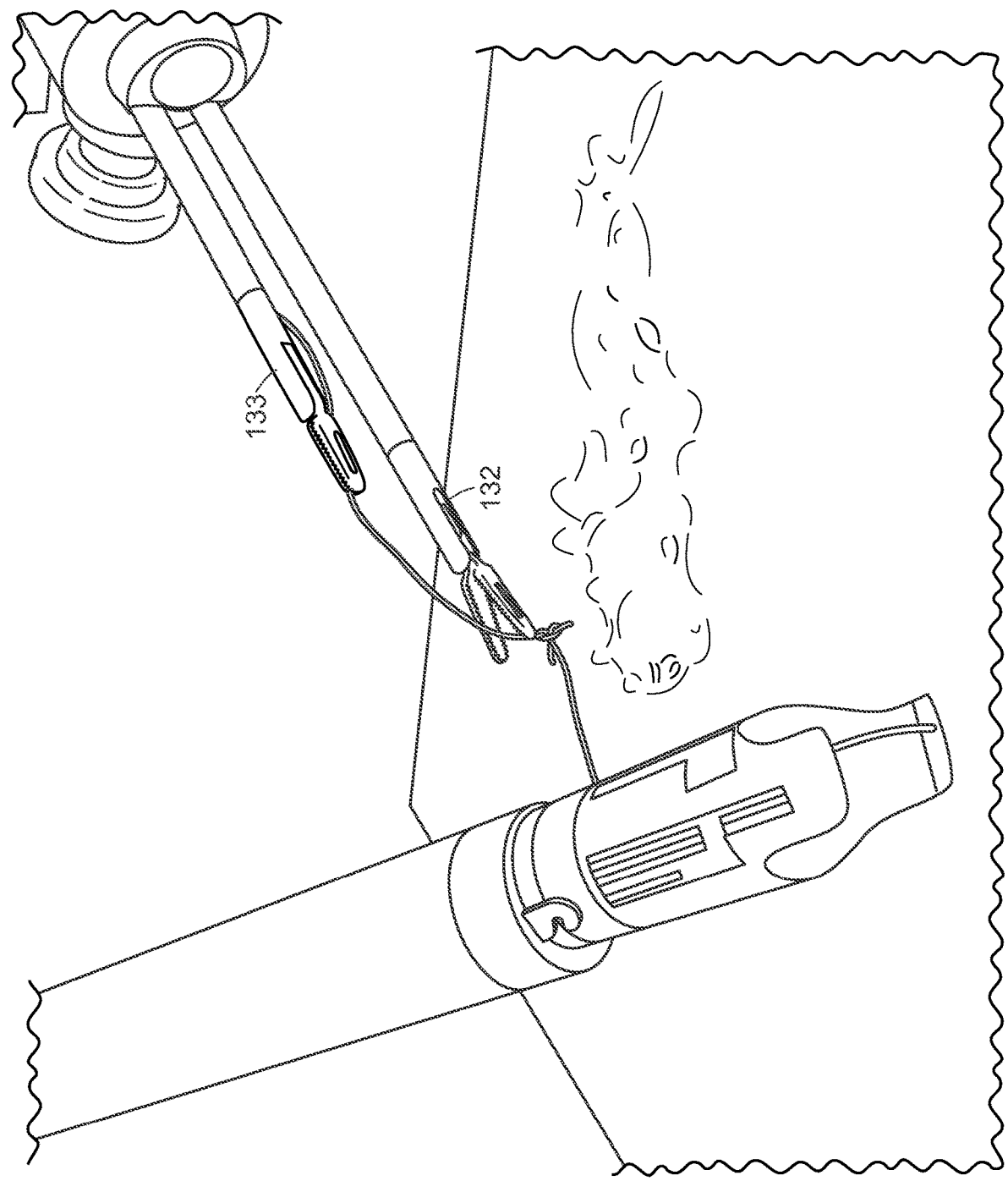
Figure 34:
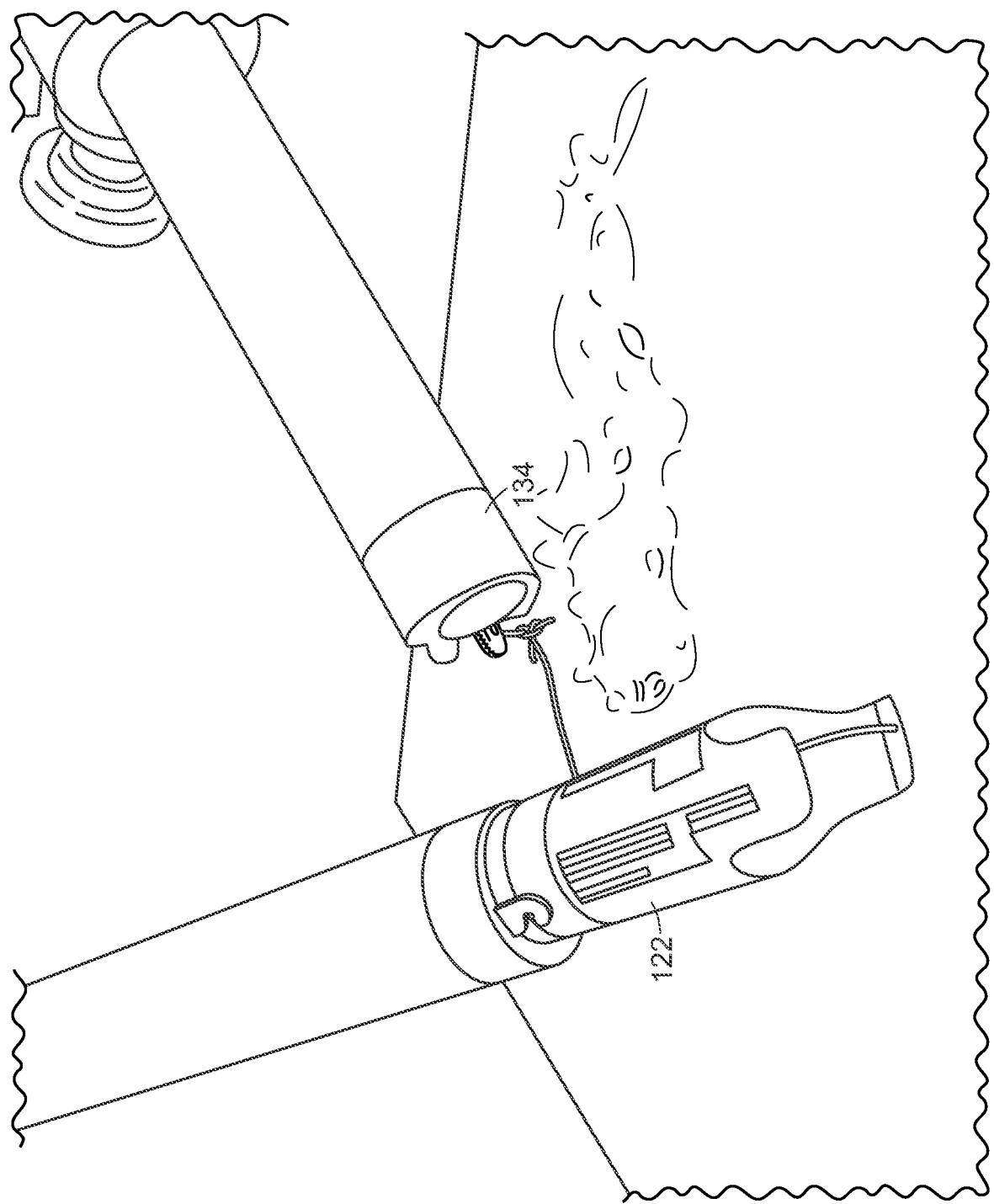

The remaining suture is cut to clean up and complete the knot. The grasper 132 is extended 55 mm and its jaws opened to grasp the suture (FIG. 33). The camera assembly 134 is extended to cut the suture (FIG. 34).

Figure 35:
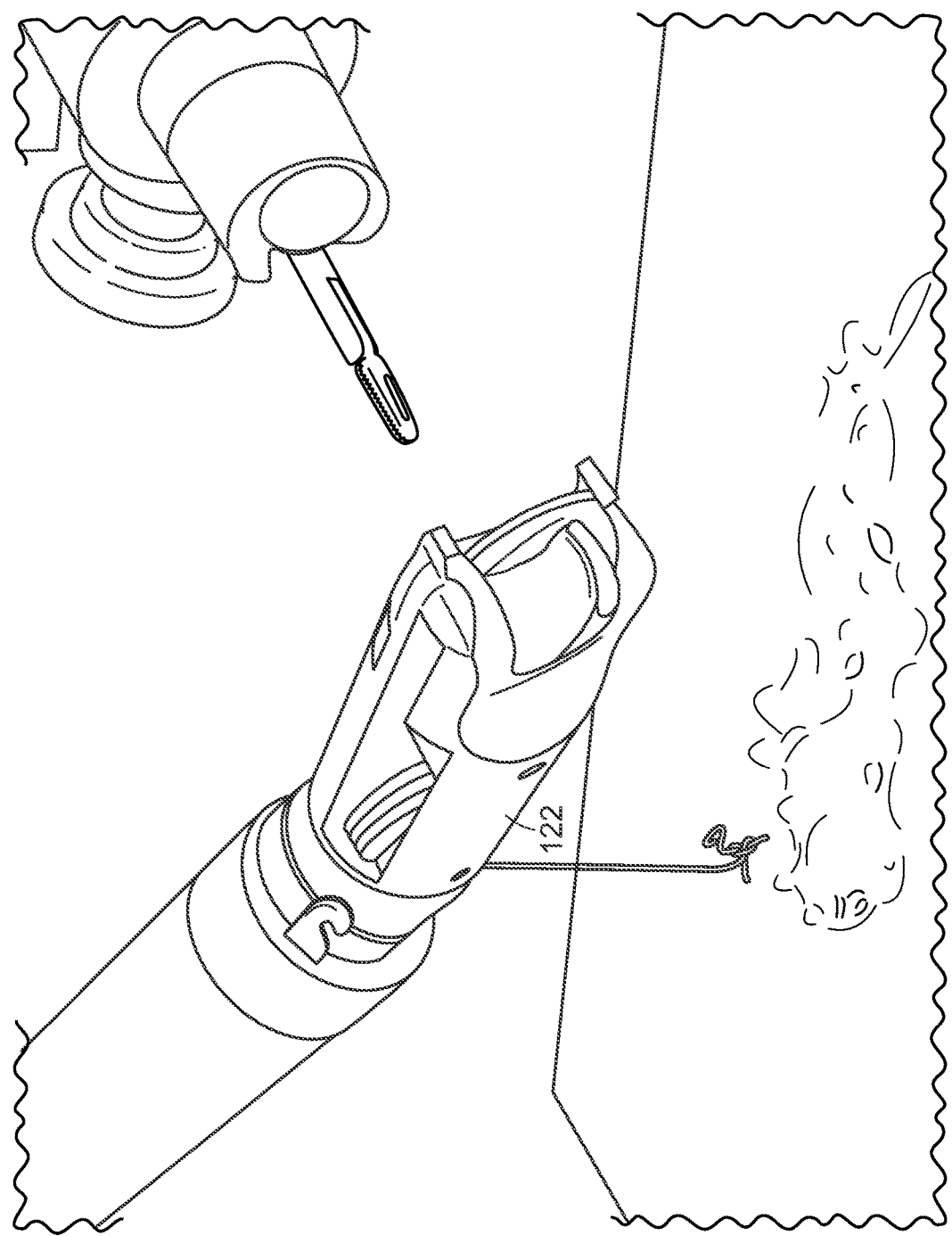

The camera assembly 134 is retracted with grasper 132. Grasper 133 is opened and also retracted to leave a completed square knot (FIG. 35).

Figure 36:
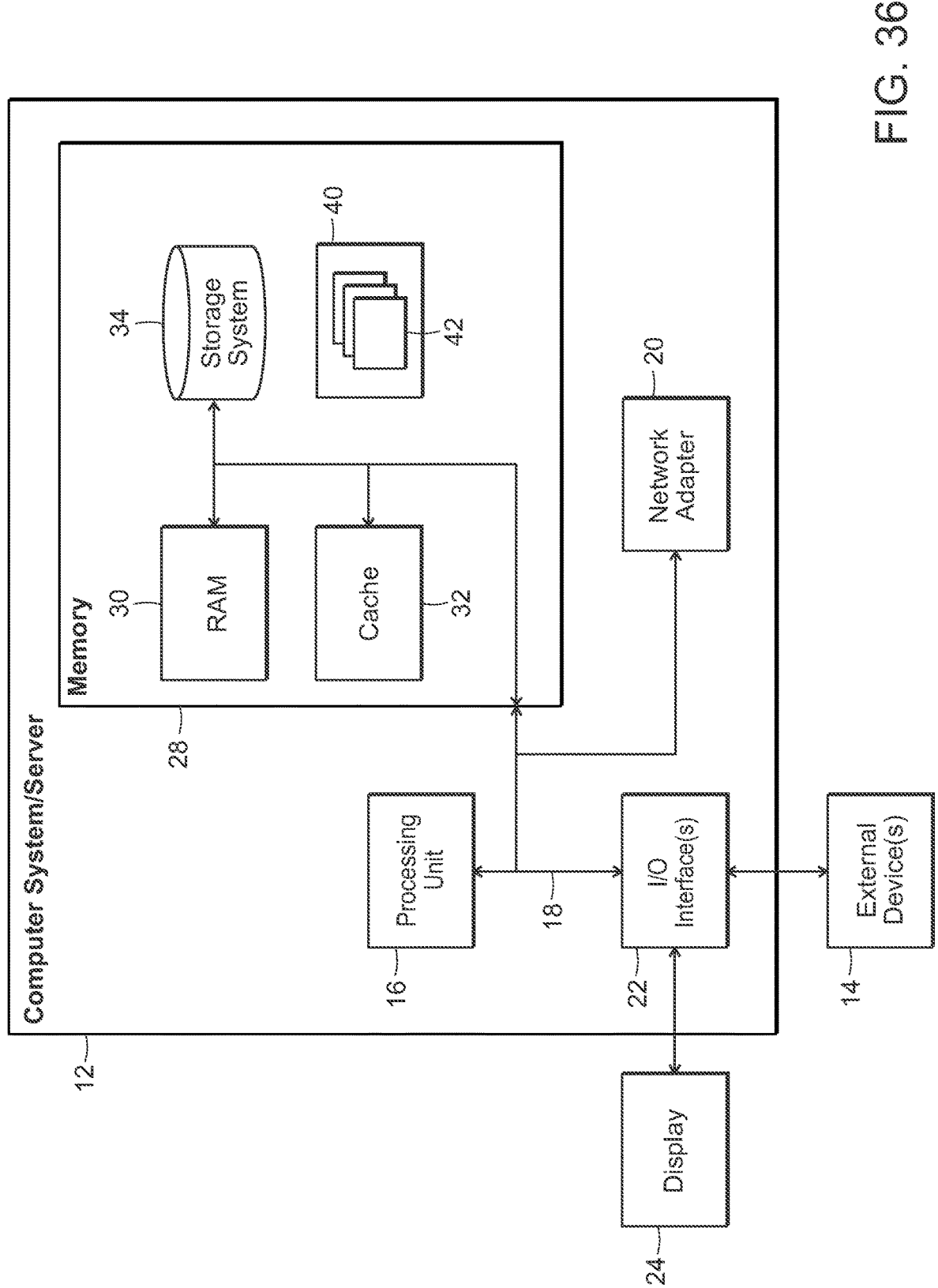
FIG. 36 is a schematic of an exemplary computing node that may be used to control operation of the robotic suturing system described herein in accordance with one or more embodiments.

Referring now to FIG. 36, a schematic of an exemplary computing node 10 is shown that may be used to control operation of the robotic suturing system described herein in accordance with one or more embodiments. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 36, computer system/server 12 in computing node 10 is shown in the form of a general-purpose computing device. The components of computer system/server 12 may include, but are not limited to, one or more processors or processing units 16, a system memory 28, and a bus 18 coupling various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure includes a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and/or block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for tying a suture knot, comprising:
    (a) throwing a stitch at a target location on a tissue of a patient using a suturing end effector to form a first suture line and a second suture line extending out of the target location;
    (b) grasping the first suture line with one of a first grasper and a second grasper and cutting the first suture line, wherein cutting the first suture line comprises grasping the first suture line using the first and second graspers at spaced apart locations and retracting the first and second graspers to engage the first suture line with a cutting blade to sever the first suture line;
    (c) manipulating the suturing end effector and the first and second graspers to tie the suture knot using the first and second suture lines; and
    (d) tightening the suture knot onto the tissue using the first and second graspers.

2. The method of claim 1, wherein steps (a)-(d) are performed autonomously.

3. The method of claim 1, further comprising tying a series of suture knots on the tissue of the patient, wherein the series of suture knots comprises the suture knot.

4. The method of claim 1, wherein the suture knot comprises a square knot.

5. The method of claim 1, wherein each of the first and second graspers comprises a jaw member pivotally connected to another jaw member, wherein manipulating the first and second graspers in (c) comprises:
    (i) positioning the jaw members of the graspers on opposite sides of a suture line;
    (ii) moving the jaw members of each grasper relative to the other jaw member on the same grasper to achieve a grasping mode position in each grasper, wherein each of the graspers fixedly holds a portion of the suture line and inhibits movement of the suture line relative to the grasper for one part of the knot tying process; and
    (iii) moving the jaw members of each grasper relative to the other jaw member of the same grasper to achieve a pulley mode position in each grasper in which the graspers slidably support the suture line at a pivot point and permit the suture line to slide relative to the graspers for another part of the knot tying process.

6. The method of claim 1, wherein the first grasper and the second grasper are extendable or retractable relative to the suturing end effector.

7. The method of claim 6, wherein the first grasper and the second grasper are independently extendable or retractable relative to each other.

8. The method of claim 1, wherein the suturing end effector comprises a suturing needle, wherein (a) comprises piercing the tissue with the suturing needle to throw the stitch at the target location.

9. The method of claim 1, wherein in (c), manipulating the first and second graspers comprises (i) moving the first grasper relative to the second grasper or (ii) moving the second grasper relative to the first grasper to tie the suture knot.

10. The method of claim 1, wherein in (c), manipulating the first and second graspers comprises extending, retracting, translating, or rotating at least one of the first grasper and the second grasper to tie the suture knot.

11. The method of claim 1, wherein in (c), manipulating the first and second graspers comprises automatically opening or closing at least one of the first grasper and the second grasper to selectively grasp or release the first suture line or the second suture line.

12. The method of claim 1, further comprising, prior to (a), articulating the suturing end effector to position the suturing end effector adjacent to or in contact with a predetermined suture start point of the target location.

13. The method of claim 12, wherein articulating the suturing end effector comprises rotating or translating the suturing end effector relative to the predetermined suture start point.

14. The method of claim 1, wherein in (a), throwing the stitch comprises firing the suturing end effector one or more times to form the first suture line and the second suture line.

15. The method of claim 1, wherein in (c), manipulating the suturing end effector comprises using the suturing end effector to grasp or engage with at least one of the first suture line and the second suture line.

16. The method of claim 15, wherein in (c), manipulating the suturing end effector comprises using an extendable hook of the suturing end effector to grasp or engage with the first suture line or the second suture line.

17. The method of claim 16, wherein in (c), manipulating the suturing end effector comprises retracting the extendable hook to lock the first suture line or the second suture line within a portion of the suturing end effector.

18. The method of claim 1, wherein (c) further comprises translating or rotating the suturing end effector to provide counter-traction for tying the suture knot.

19. The method of claim 18, wherein translating the suturing end effector comprises moving the suturing end effector away from the target location to provide the counter-traction.

\* \* \* \* \*